(12) United States Patent
Takimiya et al.

(10) Patent No.: US 9,260,451 B2
(45) Date of Patent: Feb. 16, 2016

(54) METHOD FOR PRODUCING AROMATIC COMPOUND

(71) Applicant: Nippon Kayaku Kabushiki Kaisha, Tokyo (JP)

(72) Inventors: Kazuo Takimiya, Higashihiroshima (JP); Shoji Shinamura, Tokyo (JP); Masahiro Hamada, Tokyo (JP); Yuichi Sadamitsu, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/423,516

(22) PCT Filed: Aug. 22, 2013

(86) PCT No.: PCT/JP2013/072417
§ 371 (c)(1),
(2) Date: Feb. 24, 2015

(87) PCT Pub. No.: WO2014/030700
PCT Pub. Date: Feb. 27, 2014

(65) Prior Publication Data
US 2015/0239901 A1    Aug. 27, 2015

(30) Foreign Application Priority Data

Aug. 24, 2012   (JP) ................................. 2012-185234

(51) Int. Cl.
| | |
|---|---|
| *H01L 51/00* | (2006.01) |
| *C07D 493/04* | (2006.01) |
| *C07D 495/04* | (2006.01) |
| *C07D 517/04* | (2006.01) |
| *C07D 495/22* | (2006.01) |

(52) U.S. Cl.
CPC ............ *C07D 495/22* (2013.01); *C07D 493/04* (2013.01); *C07D 495/04* (2013.01); *C07D 517/04* (2013.01); *H01L 51/0068* (2013.01); *H01L 51/0071* (2013.01); *H01L 51/0073* (2013.01); *H01L 51/0074* (2013.01)

(58) Field of Classification Search
CPC ............ H01L 51/0071; H01L 51/0073; H01L 51/0074; C07D 493/04; C07D 495/04; C07D 517/04
USPC .......................................................... 549/42
See application file for complete search history.

(56) References Cited

U.S. PATENT DOCUMENTS

| | | | |
|---|---|---|---|
| 3,278,552 A | 10/1966 | Geering | |
| 3,433,874 A | 3/1969 | Geering | |
| 2009/0001357 A1 | 1/2009 | Takimiya et al. | |
| 2009/0261300 A1 | 10/2009 | Watanabe | |
| 2010/0032655 A1 | 2/2010 | Takimiya et al. | |
| 2010/0065826 A1 | 3/2010 | Takimiya et al. | |
| 2011/0040107 A1 | 2/2011 | Goto et al. | |
| 2011/0250719 A1 | 10/2011 | Zuberi et al. | |
| 2011/0303910 A1 | 12/2011 | Kuwabara et al. | |
| 2012/0161109 A1 | 6/2012 | Wigglesworth et al. | |
| 2014/0051865 A1 | 2/2014 | Takimiya | |

FOREIGN PATENT DOCUMENTS

| | | |
|---|---|---|
| EP | 1847544 A1 | 10/2007 |
| EP | 2067782 A1 | 6/2009 |
| EP | 2077590 A1 | 7/2009 |
| EP | 2098527 A1 | 9/2009 |

(Continued)

OTHER PUBLICATIONS

International Search Report mailed Oct. 1, 2013 in co-pending PCT application No. PCT/JP2013/071120.
Written Opinion mailed Oct. 1, 2013 in co-pending PCT application No. PCT/JP2013/071120.
International Preliminary Report on Patentability mailed Feb. 26, 2015 in co-pending PCT application No. PCT/JP2013/071120.
International Search Report mailed Sep. 24, 2013 in corresponding PCT application no. PCT/JP2013/072417.
Written Opinion mailed Sep. 24, 2013 in corresponding PCT application No. PCT/JP2013/072417.
International Preliminary Report on Patentability mailed Mar. 5, 2015 in corresponding PCT application No. PCT/JP2013/072417.

(Continued)

*Primary Examiner* — Erich A Leeser
(74) *Attorney, Agent, or Firm* — Nields, Lemack & Frame, LLC

(57) ABSTRACT

A method for producing a heterocyclic compound represented by general formula (2) from a heterocyclic compound represented by general formula (1) (in the formulae, X1 represents a halogen atom; each of Y1 and Y2 independently represents an oxygen atom, sulfur atom, or selenium atom; each of R1 and R2 independently represents a substituent; m and n respectively represent the number of substituents R1 and R2, each of m and n representing an integer of 0-4; and when m and n are 2 or higher, R1 and R2 may be the same or different and may bond to each other to form an optionally substituted ring).

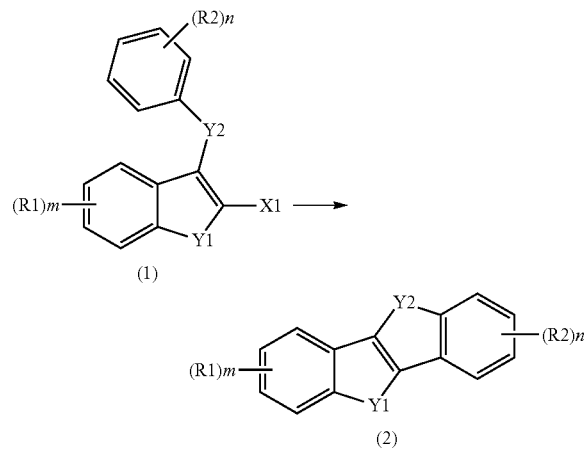

24 Claims, No Drawings

(56) References Cited

FOREIGN PATENT DOCUMENTS

| | | | |
|---|---|---|---|
| EP | 2368892 A1 | 9/2011 | |
| GB | 2465626 A | 6/2010 | |
| JP | 2005-154371 A | 6/2005 | |
| JP | 2008-239987 A | 10/2008 | |
| JP | 2008-290963 A | 12/2008 | |
| JP | 2010-202523 A | 9/2010 | |
| JP | 2010-254599 A | 11/2010 | |
| JP | 2010-275192 A | 12/2010 | |
| JP | 2011-256144 A * | 12/2011 | ........... C07D 495/04 |
| JP | 2012-1442 A | 1/2012 | |
| JP | 2012-510454 A | 5/2012 | |
| JP | 2012-134482 A | 7/2012 | |
| SU | 755785 A1 | 8/1980 | |
| WO | 2006/077888 A1 | 7/2006 | |
| WO | 2008/026602 A1 | 3/2008 | |
| WO | 2008/047896 A1 | 4/2008 | |
| WO | 2008/050726 A1 | 5/2008 | |
| WO | 2009/128559 A1 | 10/2009 | |
| WO | 2010/058692 A1 | 5/2010 | |
| WO | 2010/098372 A1 | 9/2010 | |
| WO | 2012/010292 A1 | 1/2012 | |

OTHER PUBLICATIONS

J. Am. Chem. Soc., 2007, vol. 129, pp. 15732-15733, "Highly Soluble [1]Benzothieno[3,2-b]benzothiophene (BTBT) Derivatives for High-Performance, Solution-Processed Organic Field-Effect Transistors", Ebata, et al.

Advanced Materials, 2009, vol. 21, pp. 213-216, "Dithieno[2,3-d;2'3'-d']benzo[1,2-b;4,5-b']dithiophene (DTBDT) as Semiconductor for High-Performance, Solution-Processed Organic Field-Effect Transistors", Gao, et al.

J. Org. Chem, 2005, vol. 70, pp. 1147-1153, "Synthesis and Structural, Electronic, and Optical Properties of Oligo (thienylfuran)s in Comparison with Oligothiophenes and Oligofurans", Miyata, et al.

J. Heterocyclic Chem., May-Jun. 1998, vol. 35(3), pp. 725-726, "A Simple One-Pot Synthesis of [1]Benzotelluro[3,2-b] [1]-benzotellurophenes and its Selenium and Sulfur Analogues from 2,2'-Dibromodiphenylacetylene [1]", Sashida, et al.

J. Am. Chem. Soc., 2011, vol. 133, pp. 5024-5035, "Linear- and Angular-Shaped Naphthodithiophenes: Selective Synthesis, Properties, and Application to Organic Field-Effect Transistors", Shinamura, et al.

J. Am. Chem. Soc., 2004, vol. 126, pp. 5084-5085, "2,6-Diphenylbenzo[1,2-b:4,5-b']dichalcogenophenes: A New Class of High-Performance Semiconductors for Organic Field-Effect Transistors", Takimiya, et al.

J. Am. Chem. Soc., 2006, vol. 128, pp. 12604-12605, "2,7-Diphenyl[1]benzothieno[3,2-b]benzothiophene, A New Organic Semiconductor for Air-Stable Organic Field-Effect Transistors with Mobilities up to 2.0 cm2 V-1 s-1", Takimiya, et al.

Science and Technology of Advanced Materials, 2007, vol. 8(4), pp. 273-276, "Design strategy for air-stable organic semiconductors applicable to high-performace field-effect transistors", Takimiya, et al.

J. Am. Chem. Soc., 2007, vol. 129, pp. 2224-2225, "Facile Synthesis of Highly Pi-Extended Heteroarenes, Dinaphtho [2,3-b"2',3'-f]chalcogenopheno[3,2-b]chalcogenophenes, and Their Application to Field-Effect Transistors", Yamamoto, et al.

J. Org. Chem., 2002, vol. 67, pp. 1905-1909, "Synthesis of 2,3-Disubstituted Benzo[b]thiophenes via Palladium-Catalyzed Coupling and Electrophilic Cyclization of Terminal Acetylenes", Yue, et al.

J. Org. Chem., 2005, vol. 70, pp. 10292-10296, "Synthesis of 2,3-Disubstituted Benzo[b]furans by the Palladium-Catalyzed Coupling of o-Iodoanisoles and Terminal Alkynes, Followed by Electrophilic Cyclization", Yue, et al.

Notice of Allowance mailed Jul. 16, 2015 in co-pending U.S. Appl. No. 14/421,294.

European communication dated Aug. 20, 2015 in corresponding European patent application No. EP 13830648.5.

"Aryl-Aryl Bond Formation by Transition-Metal-Catalyzed Direct Arylation", Dino Alberico et al., Chemical Reviews, vol. 107, No. 1, pp. 174-238, Jan. 2007.

* cited by examiner

METHOD FOR PRODUCING AROMATIC COMPOUND

TECHNICAL FIELD

The present invention relates to a method for manufacturing a novel aromatic compound, particularly a heterocyclic compound, and an organic semiconductor material containing the compound.

BACKGROUND ART

In recent years, organic electronic devices have drawn increasing attention. The reasons are that they have flexibility, are applicable to a large area, and make it feasible to employ a low-cost, high-speed printing process in manufacturing of electronic devices. The typical organic electronic devices include organic EL elements, organic solar cell elements, organic photoelectric conversion elements and organic transistor elements. Organic EL elements intend to be applied to flat panel displays, and have been applied to mobile phone displays through TVs and the like. Organic EL elements with higher functionality have been continuously developed. Organic solar cell elements have been used as flexible, low-cost energy sources, and organic transistor elements have been applied to flexible displays and low-cost IC's. Research and development thereof have been aggressively carried out.

In developing these organic electronic devices, it is very important to develop organic semiconductor materials constituting the devices. Acene organic semiconductors such as pentacene have been investigated as an organic transistor material. Heterocyclic compounds such as heteroacene compounds, in particular the compounds containing sulfur or selenium atoms, have been also investigated. Among them, benzothieno-benzothiophenes (e.g., DPh-BTBT and alkyl BTBT), dinaphtho-thienothiophenes (DNTT) and the like have been developed as high-performance materials with stability in atmosphere and have been proposed as compounds with excellent semiconductor characteristics and stability in comparison with pentacene (Patent Literatures 1 to 3 and Non Patent Literatures 1 to 3). Regarding methods of manufacturing these useful compounds, there are many reports. However, the methods are not satisfactory due to unsatisfactory yields and the difficulty in producing a compound with an asymmetrical structure at a high yield. Further improvement in the manufacturing method is desired.

Conventionally, many methods have been tried to synthesize [1]benzothieno[3,2-b][1]benzothiophene (hereinafter abbreviated as BTBT).

Regarding a method of synthesizing BTBT, Patent Literature 4 discloses a method of synthesizing BTBT by a reaction between α,α-dichlorotoluene and sulfur. However, a compound having a dichloromethyl group generally has many problems in availability and storage stability. Patent Literature 4 and Patent Literature 5 disclose a method of synthesizing BTBT from α,α,α-trichlorotoluene, but the method causes a very low yield of 12% and thus is not practicable. Thereafter, a synthesis method represented by the following reaction formula 1 has been developed and known. However, the method has a problem of very high production cost due to the long reaction path (Patent Literature 6).

[Formula 1]

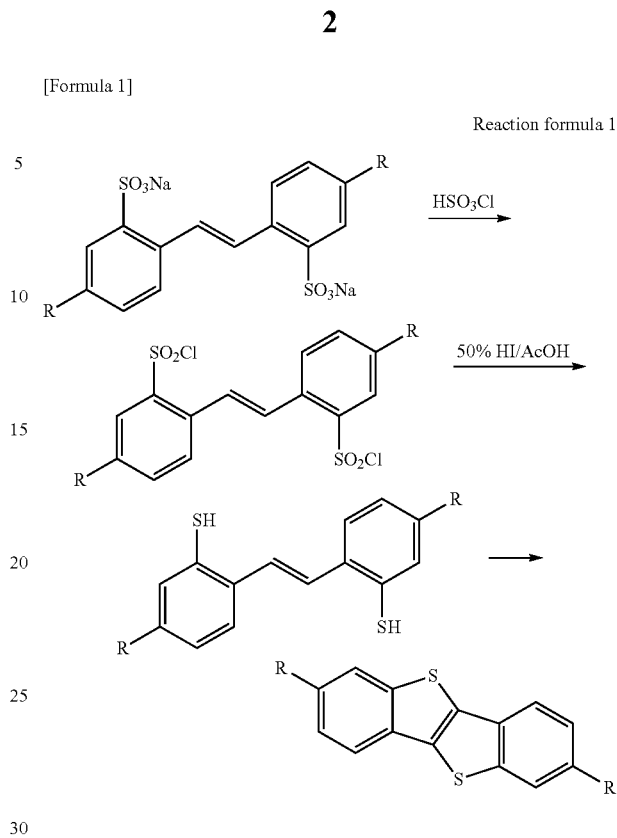

Reaction formula 1

A method of producing the compound comprising the steps of reacting 2,2'-dibromodiphenylacetylene with tert-butyl lithium at extremely low temperatures and then adding sulfur thereto has been developed. However, tert-butyl lithium, used in the method, reacts with moisture in the air to take fire. The method therefore has problems in safety and industrial applicability (Patent Literature 7 and Non Patent Literature 4).

Patent Literature 8 describes a method of synthesizing BTBT comprising diazotization of 2,7-diamino BTBT, a starting material, and diazo decomposition of the diazo BTBT. However, the synthesis of 2,7-diamino BTBT (in the reaction formula 1, R=NH$_2$) requires several reaction steps. Use of 2,7-diamino BTBT as a starting material therefore causes high cost and inefficient manufacturing methods.

BTBT may be fused with a benzene ring. As such a fused compound, for instance, dinaphtho[2,3-b:2',3'-f]thieno[3,2-b]thiophene (hereinafter abbreviated as DNTT) has been known.

It has been reported that this compound has excellent characteristics as organic semiconductor. There is therefore need to establish an industrial method of manufacturing DNTT derivatives.

Patent Literature 9 and Non Patent Literatures 3 and 5 describe a method of synthesizing DNTT through the following reaction scheme.

[Formula 2]

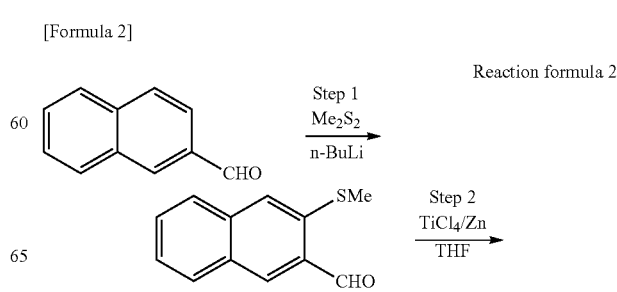

Reaction formula 2

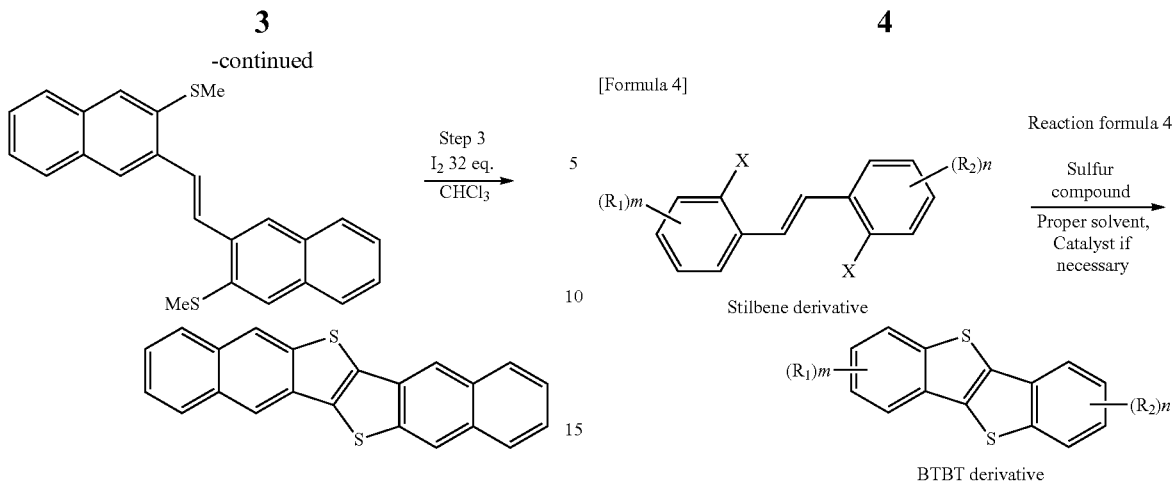

The synthesis method, however, has various problems: (1) in Step 1, use of dimethyl disulfide, i.e. a malodorous substance; (2) in Step 1, use of n-butyl lithium, i.e. a water prohibitive substance; (3) in Step 3, a large amount of iodine and the like are required and reaction efficiency is extremely low; and (4) by-products such as methyl iodide, i.e. a deleterious substance are generated, which cause environmental problems.

In view of the foregoing, it is extremely difficult to industrially produce BTBT derivatives (including DNTT derivatives). Further improved manufacturing methods have been therefore investigated.

Patent Literature 10 discloses a method of synthesizing BTBT wherein an aromatic aldehyde is used as a starting material, and in Patent Literature 11 discloses a method of synthesizing BTBT wherein a halogeno-aromatic aldehyde is used as a starting material. These methods allow BTBT derivatives (including DNTT derivatives) to be synthesized in one step from an aromatic aldehyde (refer to the following reaction formula 3).

[Formula 3]

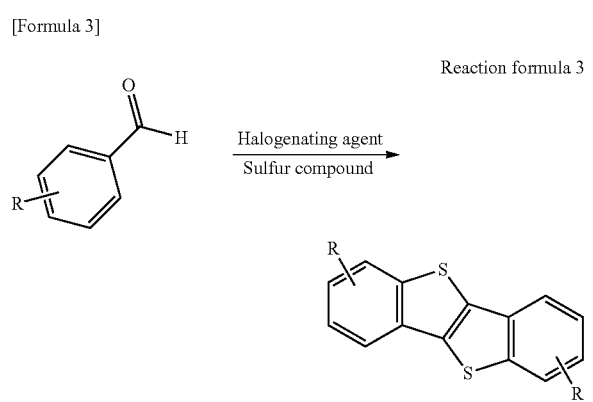

Patent Literature 12 discloses a method of synthesizing BTBT from stilbene derivatives. This method allows stilbene derivatives having various substituents to be employed as a starting material, and allows a sulfur atom to be selectively introduced to the position of a leaving group X of a stilbene derivative, thereby determining the condensation position. Consequently, BTBT derivatives (including DNTT derivatives) can be relatively easily synthesized at a high yield (refer to the following reaction formula 4).

[Formula 4]

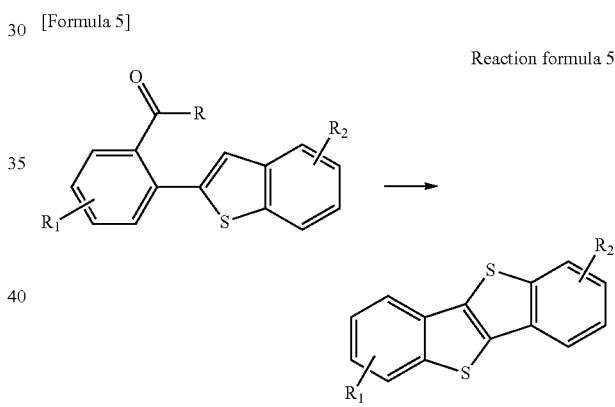

Further, Patent Literature 13 and Non Patent Literature 6 disclose that BTBT derivatives can be produced by intramolecular cyclization reaction of a precursor obtained by Stille coupling with an acid, and dealkylation of the obtained alkyl intermediate (refer to the following reaction formula 5). However, these methods cause high cost to produce the intermediate and also have the problem that producible compounds are limited

[Formula 5]

As described above, it can be easily presumed that BTBT derivatives (including DNTT derivatives) are a group of compounds having excellent characteristics. Industrial manufacturing methods thereof still are being investigated.

CITATION LIST

Patent Literature

Patent Literature 1: International Publication No. WO2006/077888
Patent Literature 2: International Publication No. WO2008/047896
Patent Literature 3: International Publication No. WO2008/050726
Patent Literature 4: U.S. Pat. No. 3,278,552
Patent Literature 5: U.S. Pat. No. 3,433,874
Patent Literature 6: U.S. Pat. No. 755,785
Patent Literature 7: International Publication No. WO2006/077888
Patent Literature 8: JP 2008-239987 A Patent Literature 9: International Publication No. 2008/050726
Patent Literature 10: JP 2008-290963 A
Patent Literature 11: JP 2010-275192 A
Patent Literature 12: JP 2010-202523 A
Patent Literature 13: JP 2011-256144 A Non Patent Literature Non Patent Literature 1: Journal of the American Chemical Society, 2006, 128, 12604
Non Patent Literature 2: Journal of the American Chemical Society, 2007, 129, 15732.
Non Patent Literature 3: Journal of the American Chemical Society, 2007, 129, 2224.
Non Patent Literature 4: Journal of Heterocyclic Chemistry (1998), 35(3), 725-726.
Non Patent Literature 5: Science and Technology of Advanced Materials (2007), 8(4), 273-276.
Non Patent Literature 6: Advanced Materials (2009), 21, 213.
Non Patent Literature 7: Journal of Organic Chemical Society, 2005, 70, 1147.
Non Patent Literature 8: Journal of Organic Chemical Society, 2002, 67, 1905.
Non Patent Literature 9: Journal of Organic Chemical Society, 2005, 70, 10292.

SUMMARY OF INVENTION

Technical Problem

An object of the present invention relates to a method of manufacturing a heterocyclic compound. More specifically, the object is to provide a manufacturing method capable of more simply and easily obtaining a heterocyclic compound represented by the formula (2) in high purity, which is useful for organic electronic devices.

Solution to Problem

As a solution to the above problems, the present inventors have found a new and convenient manufacturing method of aromatic compounds, thereby achieving the present invention.

The present invention is as follows:

[1] A method of manufacturing a heterocyclic compound represented by the general formula (2) from a heterocyclic compound represented by the general formula (1):

[Formula 6]

(1)

[Formula 7]

(2)

wherein X1 represents a halogen atom, Y1 and Y2 each independently represent an oxygen atom, a sulfur atom, or a selenium atom, R1 and R2 each independently represent a substituent, m and n each independently represent the number of substituents R1 and R2, being an integer of 0 to 4, and when m and n are each two or more, one of R1's and one of R2's may be each the same as or different from one another, or may each be linked to one another so as to form a ring which may have a substituent.

[2] The method according to [1], wherein the compound represented by the general formula (1) is obtained from a compound represented by the general formula (3):

[Formula 7]

(3)

wherein Z1 represents a leaving group or a hydrogen atom, Y1 and Y2 each independently represent an oxygen atom, a sulfur atom, or a selenium atom, R1 and R2 each independently represent a substituent, m and n each independently represent the number of substituents R1 and R2, being an integer of 0 to 4, and when m and n are each two or more, one of R1's and one of R2's may be each the same as or different from one another, or may be each linked to one another so as to form a ring which may have a substituent.

[3] The method according to [2], wherein the compound represented by the general formula (3) is obtained by reacting a compound represented by the general formula (4) and a compound represented by the general formula (5):

[Formula 8]

(4)

(5)

wherein Y1 and Y2 each independently represent an oxygen atom, a sulfur atom, or a selenium atom, R1 and R2 each independently represent a substituent, R3 represents a lower alkyl group, Z2 represents a leaving group, X2 represents a halogen atom, m and n each independently represent the number of substituents R1 and R2, being an integer of 0 to 4, and when m and n are each two or more, one of R1's and one of R2's may be each the same as or different from one another, or may be each linked to one another so as to form a ring which may have a substituent.

[4] The method according to any one of [1] to [3], wherein Y1 and Y2 each independently represent a sulfur atom or a selenium atom.

[5] The method according to any one of [1] to [4], wherein R1 and R2 are independently selected from the group consisting of a hydrogen atom, an alkyl group which may have a substituent, an aryl group which may have a substituent, an alkoxyl group which may have a substituent, a halogen atom, a nitro group, and a cyano group.

[6] The method according to any one of [1] to [4], wherein R1 and R2 are linked to each other so as to form a ring which may have a substituent.

[7] The method according to [6], wherein the ring formed by linking R1 and R2 to each other which may have a substituent is a benzene ring which may have a substituent or a naphthalene ring which may have a substituent.

[8] A heterocyclic compound obtained by the method according to any one of [1] to [7].

[9] An organic semiconductor material comprising the heterocyclic compound according to [8].

Advantageous Effects of Invention

The manufacturing method according to the present invention is an industrially applicable method of simply and easily manufacturing a heterocyclic compound of the formula (2) at a high yield, in particular, a high-purity asymmetric heterocyclic compound at a high yield.

DESCRIPTION OF EMBODIMENTS

The present invention is described in detail in the following. In the manufacturing method of the present invention, a compound represented by the formula (2) is manufactured from a compound represented by the formula (1).

[Formula 9]

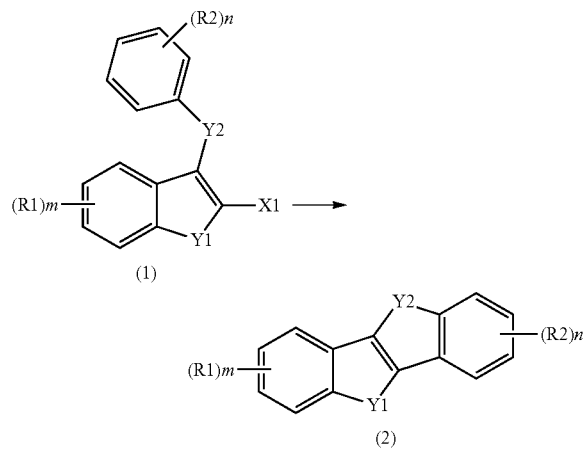

In the formula (1) and the formula (2), X1 represents a halogen atom, Y1 and Y2 each independently represent an oxygen atom, a sulfur atom, or a selenium atom, R1 and R2 each independently represent a substituent, m and n each independently represent the number of substituents R1 and R2, being an integer of 0 to 4, and when m and n are 2 or more, R1 and R2 may be the same or different from each other, and may be linked to each other so as to form a ring which may have a substituent.

Examples of the halogen atom as X1 include a fluorine atom, a chlorine atom, a bromine atom and an iodine atom, preferably a bromine atom and an iodine atom, more preferably an iodine atom. Y1 and Y2 each independently represent an oxygen atom, a sulfur atom or a selenium atom, preferably a sulfur atom or a selenium atom.

R1 and R2 each independently represent a substituent of a compound represented by the formula (2). R1 and R2 preferably represent a hydrogen atom, a hydroxyl group, an alkyl group which may have a substituent, an aryl group which may have a substituent, an alkoxyl group which may have a substituent, a halogen atom, a nitro group and a cyano group. They more preferably represent an alkyl group which may have a substituent, an aryl group which may have a substituent, a halogen atom and a nitro group. Examples of the alkyl group include a saturated or unsaturated, linear, branched or cyclic alkyl group, preferably having a carbon number of 1 to 20. Examples of the saturated or unsaturated, linear or branched alkyl group include a methyl group, an ethyl group, a propyl group, an isopropyl group, an n-butyl group, an isobutyl group, an allyl group, a t-butyl group, an n-pentyl group, an n-hexyl group, an n-octyl group, an n-decyl group, an n-dodecyl group, an n-stearyl group and an n-butenyl group. Examples of the cycloalkyl group include a C3-12 cycloalkyl group such as a cyclohexyl group, a cyclopentyl group, an adamantyl group and a norbornyl group. Among them, a saturated straight-chain alkyl group is preferred. The alkyl moiety of an alkoxyl group may be the same as the alkyl group described above. Examples of the halogen atom include a fluorine atom, a chlorine atom, a bromine atom and an iodine atom. Examples of the aryl group include an aromatic hydrocarbon group such as a phenyl group, a naphthyl group, an anthryl group, a phenanthryl group, a pyrenyl group and a benzopyrenyl group; a heterocyclic group such as a pyridyl group, a pyrazyl group, a pyrimidyl group, a quinolyl group, an isoquinolyl group, a pyrrolyl group, an indolenyl group, an imidazolyl group, a carbazolyl group, a thienyl group, a furyl group, a pyranyl group and a pyridonyl group; and a condensed heterocyclic group such as a benzoquinolyl group, an anthraquinolyl group, a benzothienyl group and a benzofuryl group. Among these, a phenyl group, a naphthyl group, a pyridyl group and a thienyl group are preferred, and a phenyl group is most preferred. Examples of "a substituent" which the alkyl group, the aryl group and the alkoxyl group may include, but not be limited to, an alkyl group, an aryl group and a halogen atom, which may be respectively the same as the alkyl group, the aryl group and the halogen atom described above.

The substitution position of R1 and R2 is not particularly limited. Each of the numbers of R1 and R2, i.e. m and n, may be 0 to 4, though not being particularly limited. When the number is 2 or more, two or more kinds of substituents may be present together.

R1 and R2 may link between R1's or between R2's so as to form a ring which may have a substituent. The ring to be formed is preferably a benzene ring or a naphthalene ring, each of which may have a substituent. The substituent may be the same as those recited as R1 and R2, preferably an alkyl group which may have a substituent, an aryl group which may have a substituent, a halogen atom and a nitro group.

A compound represented by the general formula (1) is preferably obtained from the general formula (3), for instance, in accordance with the scheme as mentioned below.

[Formula 10]

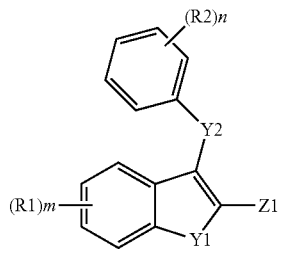
(3)

In the general formula (3), Y1, Y2, R1, R2, m, and n may be the same as defined above. Z1 represents a leaving group or a hydrogen atom. Examples of the leaving group include a trialkylsilyl group, an alkyl group and an ester group, preferably a trialkylsilyl group. Examples of the alkyl group include a methyl group, an ethyl group, an n-butyl group, an isobutyl group and a tert-butyl group, preferably a tert-butyl group. Examples of the trialkylsilyl group include a trimethylsilyl group, a triethylsilyl group, a tri-isopropylsilyl group, a tri-tert-butylsilyl group and a triphenylsilyl group, preferably a trimethylsilyl group. Examples of the ester group include a mesylate, a tosylate, and a fluorosulfonic acid ester, preferably a tosylate.

A compound represented by the general formula (3) is preferably obtained by a reaction of the general formula (4) and the general formula (5).

[Formula 11]

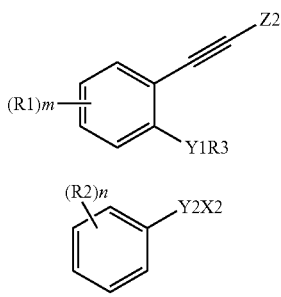
(4)

(5)

In the general formulae (4) and (5), Y1, Y2, R1, R2, m, and n may be the same as defined above. X2 represents a halogen atom, of which examples include a fluorine atom, a chlorine atom, a bromine atom and an iodine atom, preferably a chlorine atom and a bromine atom, more preferably a chlorine atom. Z2 represents a leaving group. The leaving group as Z2 may be the same as recited in Z1. R3 represents a lower alkyl group. The lower alkyl group means an alkyl group having a carbon number of 1 to 5, of which examples include a methyl group, an ethyl group, a propyl group, an isopropyl group, an n-butyl group, an isobutyl group, an allyl group, a t-butyl group and an n-pentyl group, preferably a methyl group, an ethyl group and a propyl group, most preferably a methyl group.

Examples of a compound represented by the general formula (2) are shown in the following, though not being limited thereto.

[Formula 12]

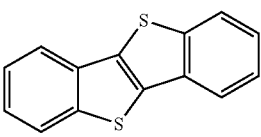
(2-1)

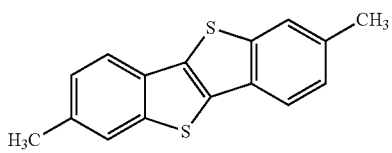
(2-2)

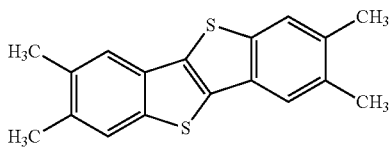
(2-3)

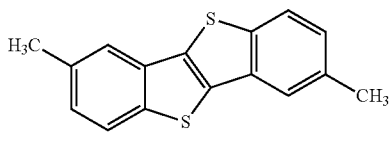
(2-4)

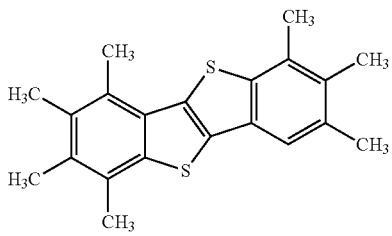
(2-5)

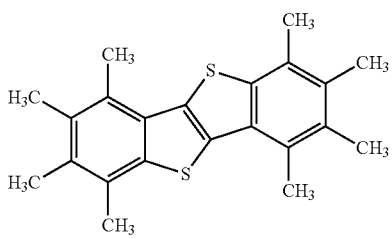
(2-6)

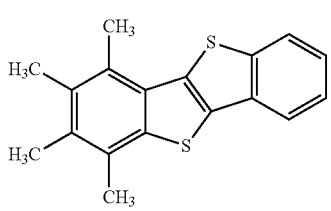
(2-7)

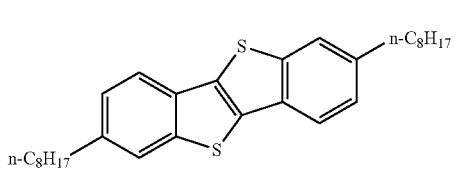
(2-8)

-continued
(2-9) 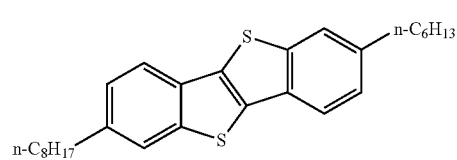
(2-10) 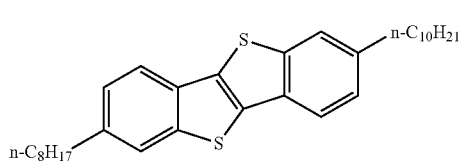
(2-11) 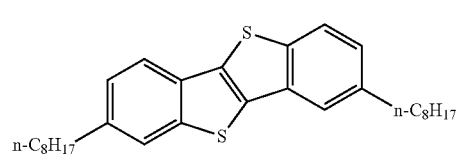
(2-12) 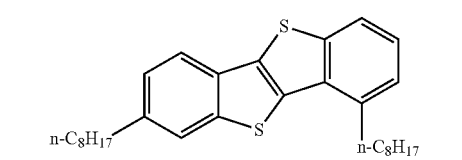
[Formula 13]
(2-13) 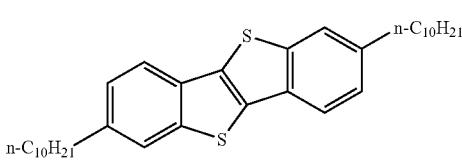
(2-14) 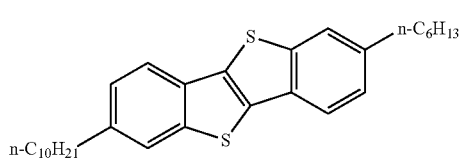
(2-15) 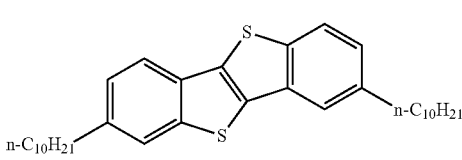
(2-16) 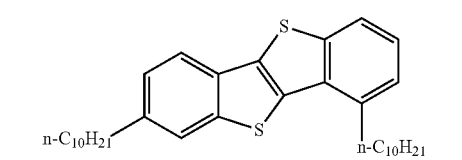
(2-17) 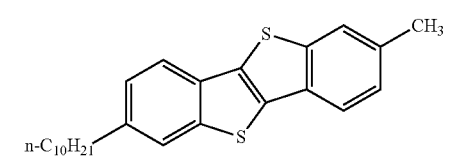
(2-18) 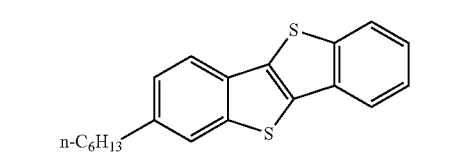
-continued
(2-19) 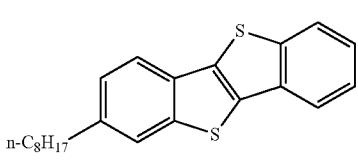
(2-20) 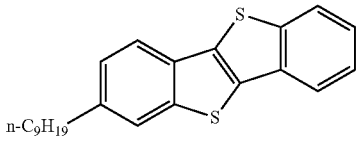
(2-21) 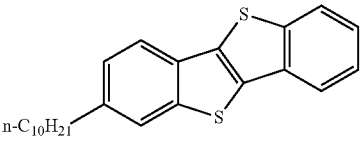
(2-22) 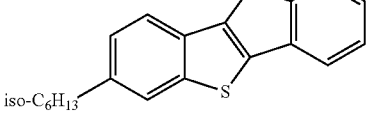
(2-23) 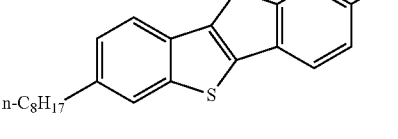
(2-24) 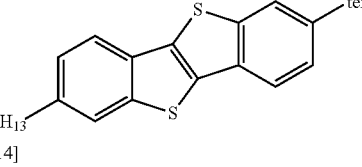
[Formula 14]
(2-25) 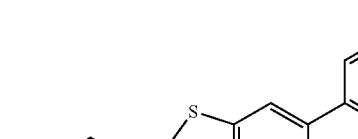
(2-26) 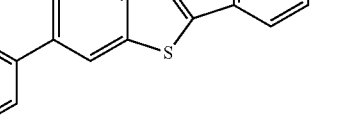

(2-27)
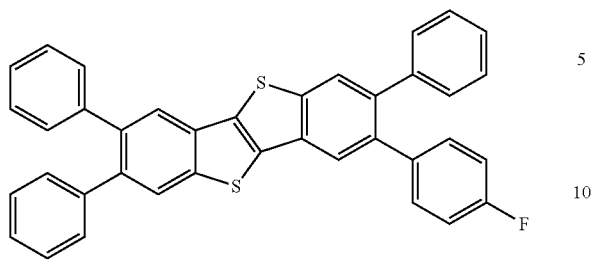
(2-28)
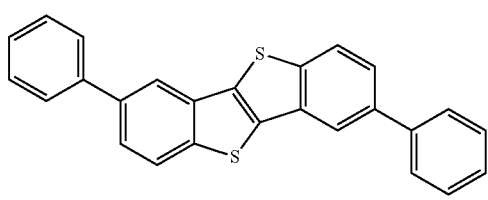
(2-29)
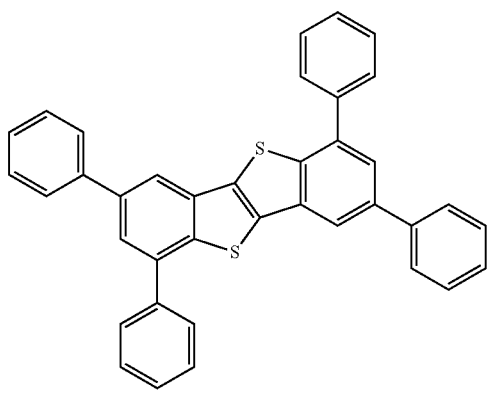
(2-30)
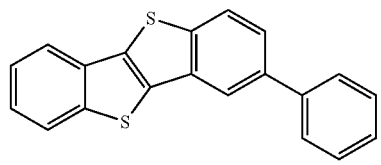
(2-31)
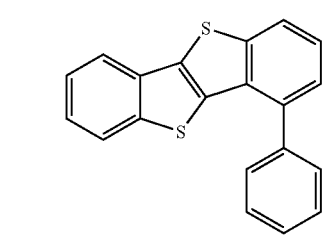
(2-32)
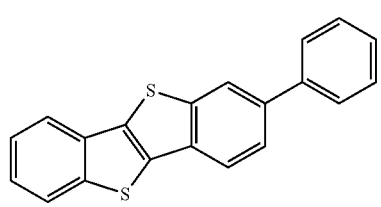
(2-33)
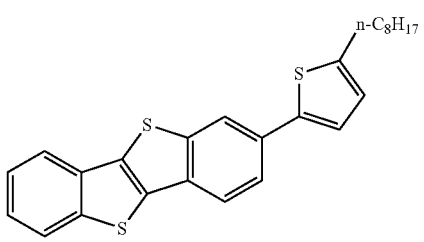
(2-34)
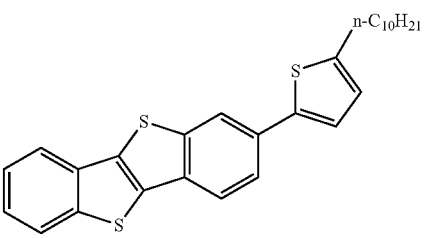
(2-35)
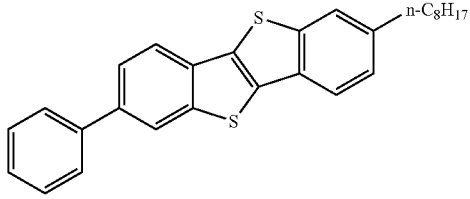
(2-36)
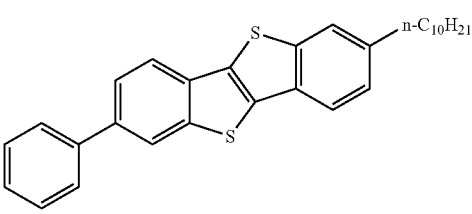
[Formula 15]
(2-37)
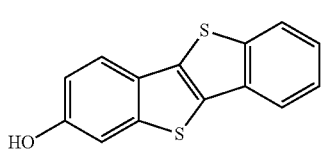
(2-38)
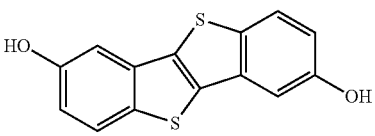
(2-39)
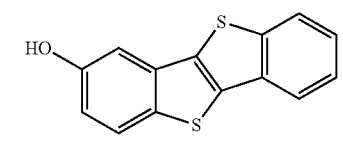
(2-40)
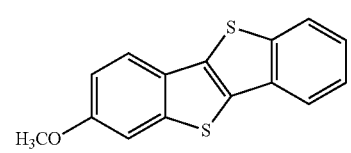

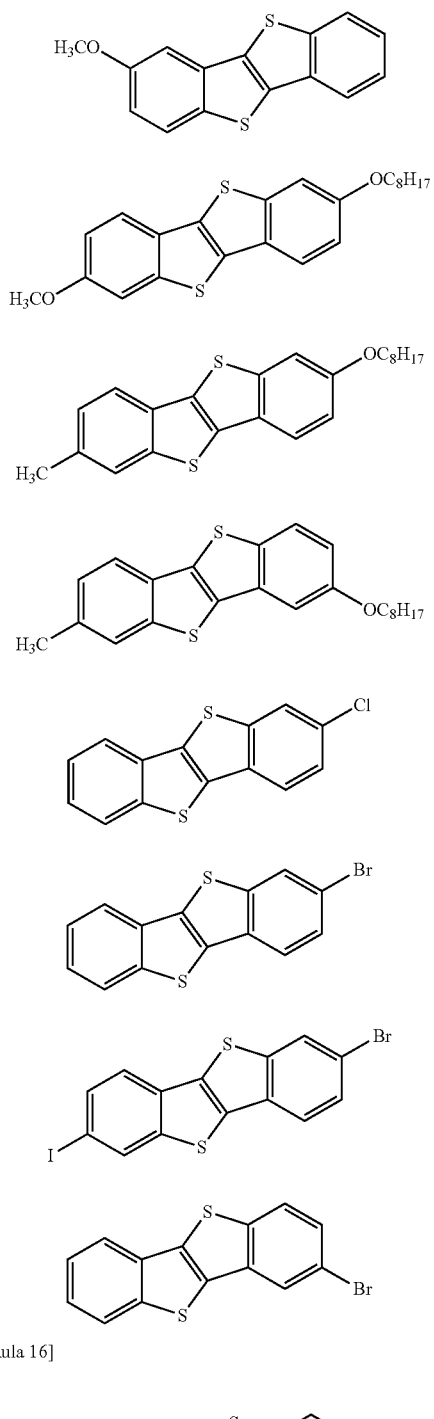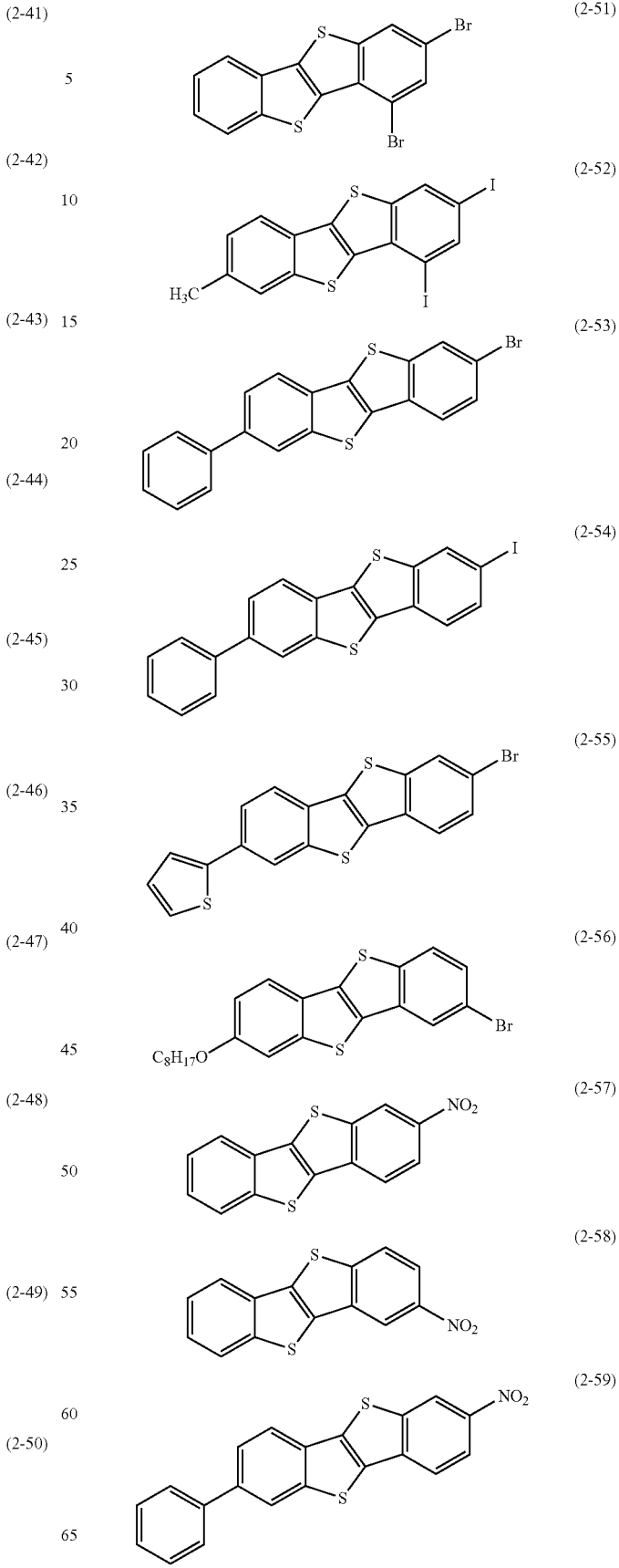

-continued
(2-60)
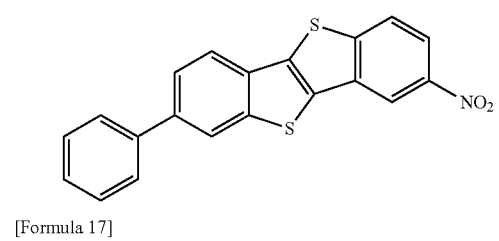
[Formula 17]
(2-61)
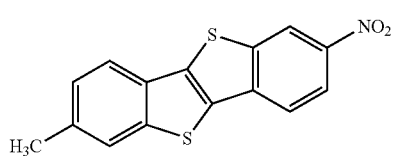
(2-62)
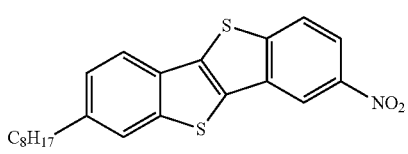
(2-63)
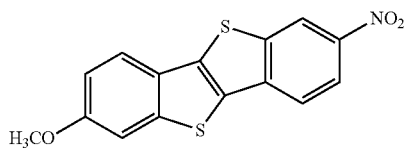
(2-64)
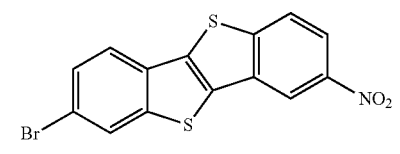
(2-65)
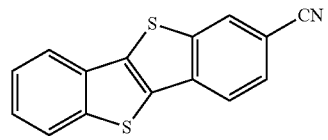
(2-66)
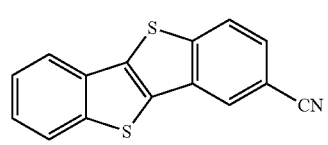
(2-67)
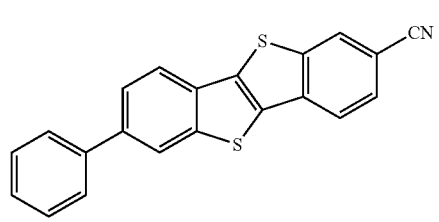
(2-68)
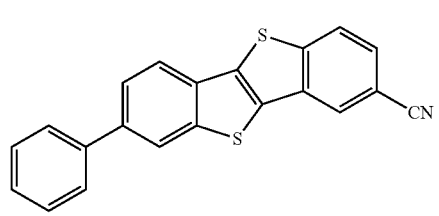
-continued
(2-69)
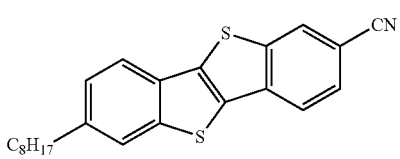
(2-70)
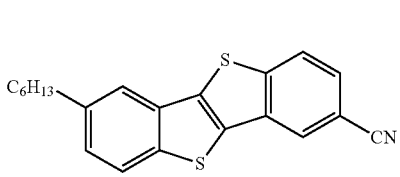
(2-71)
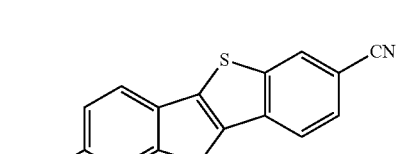
(2-72)
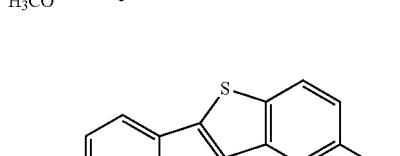
[Formula 18]
(2-73)
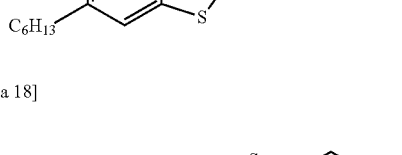
(2-74)
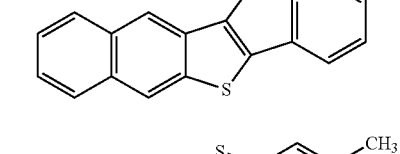
(2-75)
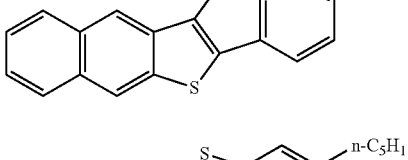
(2-76)
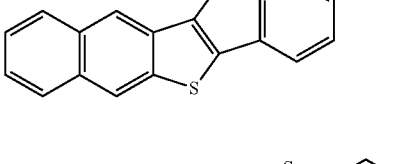
(2-77)
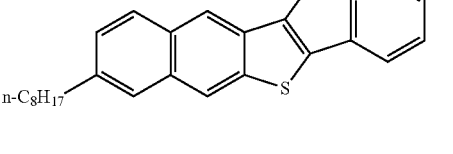

(2-78)
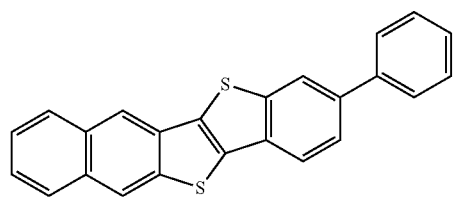
(2-79)
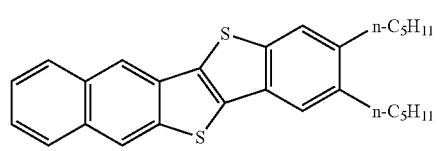
(2-80)
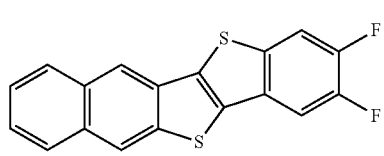
(2-81)
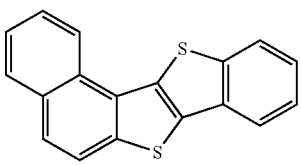
(2-82)
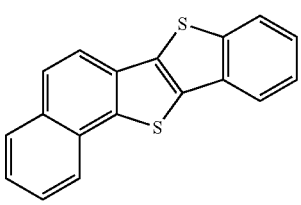
(2-83)
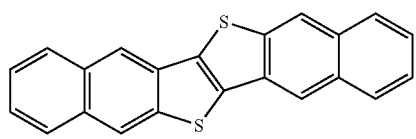
(2-84)
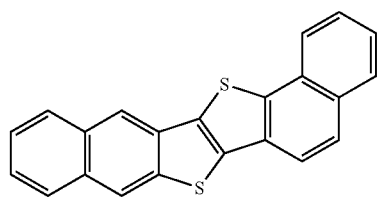
[Formula 19]
(2-85)
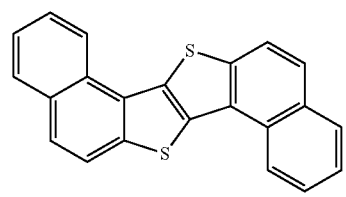
(2-86)
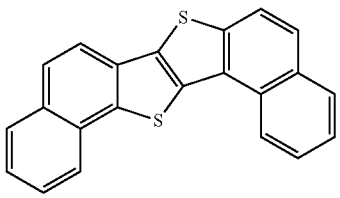
(2-87)
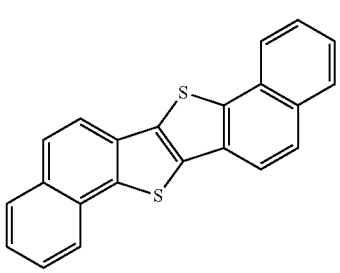
(2-88)
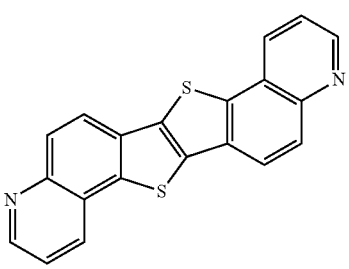
(2-89)
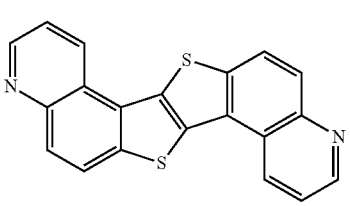
(2-90)
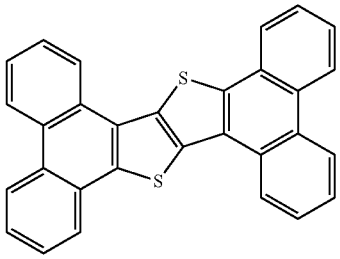
(2-91)
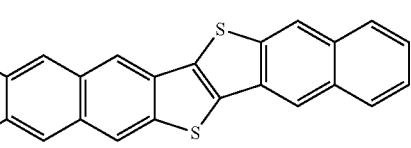
(2-92)
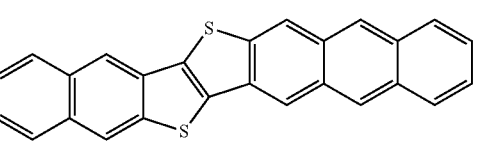

(2-93)
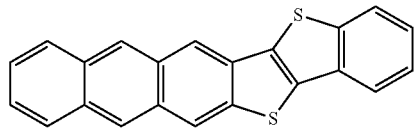
(2-94)
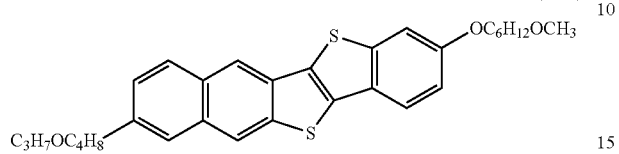
(2-95)
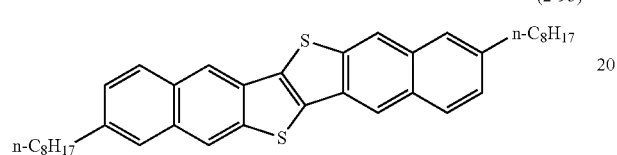
(2-96)
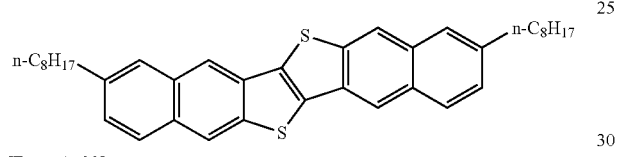
[Formula 20]
(2-97)
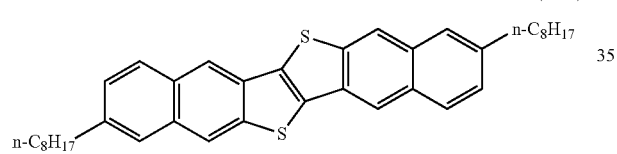
(2-98)
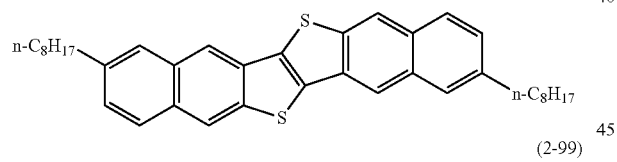
(2-99)
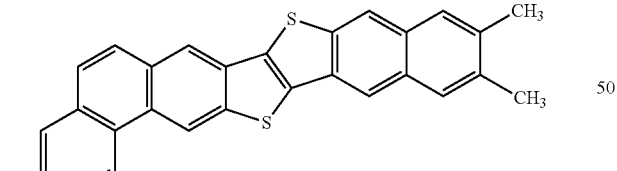
(2-100)
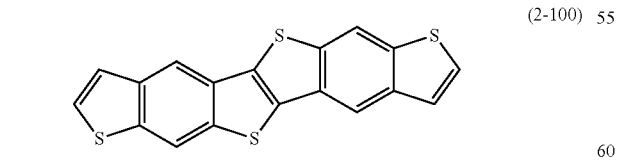
(2-101)
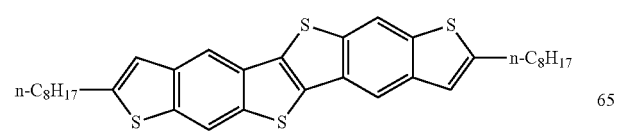
(2-102)
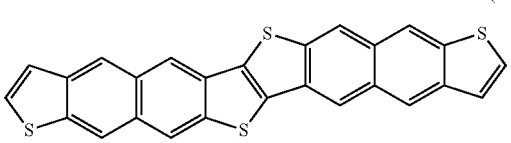
(2-103)
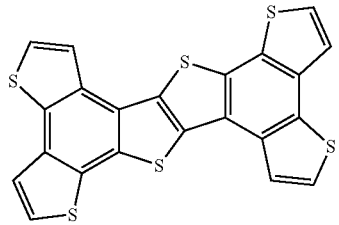
(2-104)
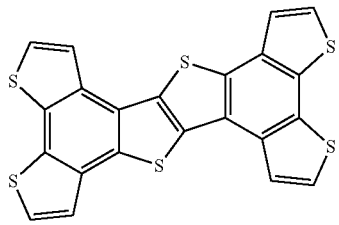
(2-105)
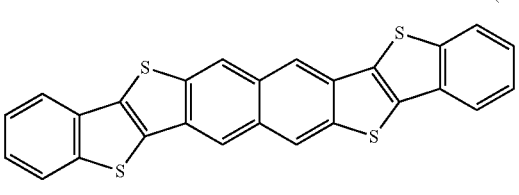
(2-106)
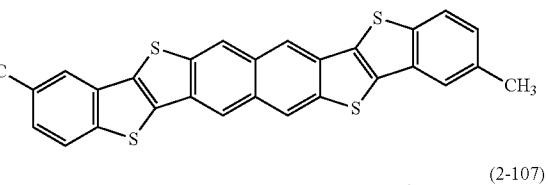
(2-107)
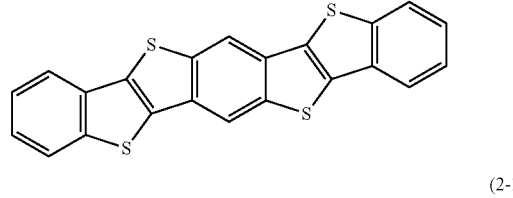
(2-108)
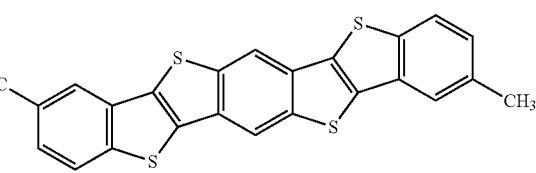
(2-109)
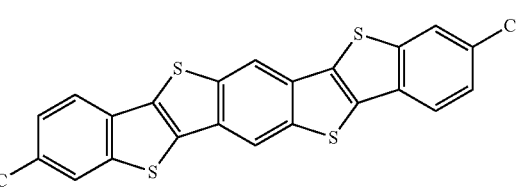

[Formula 21]

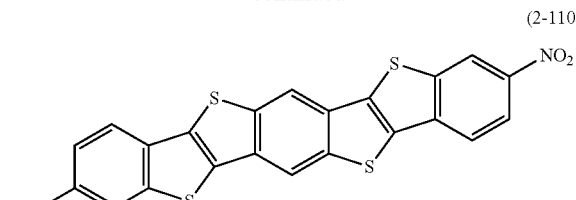 (2-110)

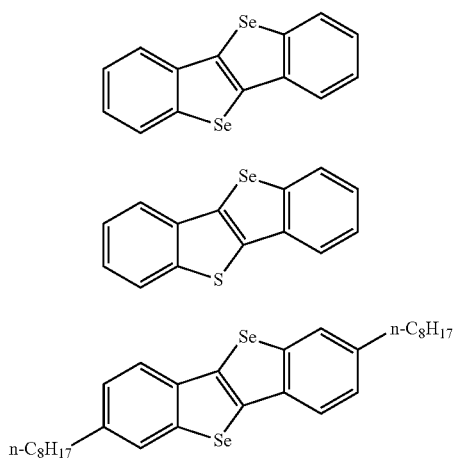 (2-111) (2-112) (2-113) (2-114) (2-115) (2-116)

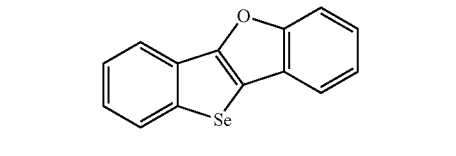 (2-117)

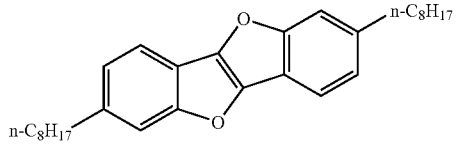 (2-118)

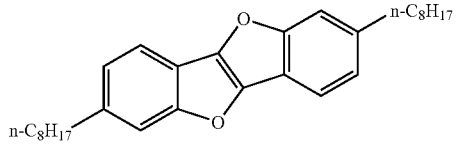 (2-119)

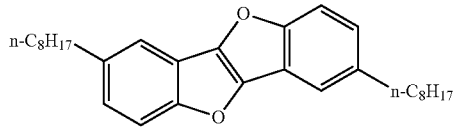 (2-120)

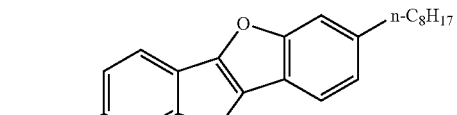 (2-121)

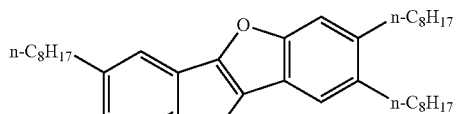 (2-122)

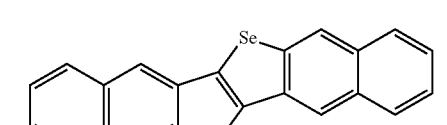 (2-123)

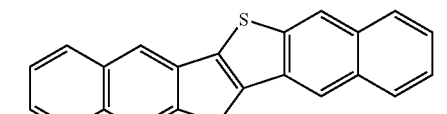 (2-124)

In manufacturing a heterocyclic compound represented by the general formula (2) of the present invention, the compound can be obtained by subjecting a compound of the general formula (1) to an intramolecular cyclization reaction based on the Mizoroki-Heck reaction. When there exist two or more reaction sites in a molecule, the cyclization reactions can be caused at the two or more sites in parallel. More specifically, a compound of the general formula (1) is reacted in a solvent or without solvent in the presence of a catalyst and if necessary in the presence of a base.

In this process, the catalyst is preferably a palladium catalyst such as $PdCl_2(PPh_3)_2$, $Pd(PPh_3)_4$, $Pd(OAc)_2$ and $PdCl_2$. The amount of the catalyst is not particularly limited to but may be 0.001 to 1 mol, preferably 0.01 to 0.5 mol, more preferably 0.05 to 0.2 mol, relative to 1 mol of a compound of the general formula (1). When there exist two reaction sites, 2 times the molar amount of catalyst may be used. Phosphine ligands such as triphenylphosphine may be also used.

Examples of the base include an inorganic base such as sodium acetate, potassium acetate and potassium carbonate; and an organic base such as triethylamine, diisopropylethylamine, tributylamine, pyridine, quinoline and ammonia. An inorganic base such as sodium acetate and potassium acetate is preferred. The amount of the base is not particularly limited as long as the necessary amount for the reaction is provided, but may be normally 0.1 to 100 mol, preferably 0.5 to 50 mol, more preferably 1 to 10 mol, relative to 1 mol of a compound of the general formula (1). In the case that the base is liquid, it can be used also as a reaction solvent.

Examples of the reaction solvent for use in performing the reaction include ethers such as diethyl ether, anisole and tetrahydrofuran; amides such as dimethylacetamide and dimethylformamide; nitriles such as acetonitrile, propionitrile and benzonitrile; and alcohols such as methanol, ethanol and butanol. Ethers such as tetrahydrofuran and amides such as dimethylacetamide are preferred. The amount of the solvent is not particularly limited but may be about 0 to 10000 mol relative to 1 mol of a compound of the general formula (1).

The reaction may be implemented at a temperature of −50° C. to 300° C. The reaction temperature may be, as appropriate, changed in this range. The range is preferably 0° C. to 250° C., more preferably 10° C. to 200° C. In this reaction, the reaction time is normally 10 minutes to 1000 hours, preferably 30 minutes to 100 hours, more preferably 30 minutes to 24 hours. In order to complete the reaction in a short time, the reaction temperature, the catalyst, the base, and the amount of the solvent may be adjusted.

If necessary, a substance of interest may be isolated from a reaction mixture and purified by known isolation and purification methods. A high-purity compound is required for use as an organic semiconductor in many cases. In that case, known methods such as recrystallization, column chromatography and vacuum sublimation purification may be employed. As appropriate, the methods may be combined for purification.

A compound represented by general formula (1) can be obtained by halogenation of a compound of the general formula (3). When there exist two or more reaction points in a molecule, halogenation reactions may be implemented at two or more sites in parallel.

The halogenation method is not particularly limited, but may be preferably a method of producing a compound of the general formula (1) by subjecting a compound of the formula (3) wherein $Z_1$ is a leaving group to a reaction with a halogenating agent, if necessary in the presence of solvent, for example, as described in Non Patent Literature 7. In this reaction, examples of the halogenating agent include a compounds containing at least one of a fluorine atom, a chlorine atom, a bromine atom and an iodine atom. Among them, a bromine atom or an iodine atom is preferred.

Examples of the halogenating agent specifically include, but not limited to, fluorine, chlorine, bromine, iodine, phosphorus trichloride, phosphorus tribromide, carbon tetrachloride, carbon tetrabromide, N-chlorosuccinimide, N-bromosuccinimide, N-iodosuccinimide, N,N-dichlorourea, sodium bromate, periodic acid, 1,3-dichloro-5,5-dimethyl hydantoin, 1,3-diiodo-5,5-dimethyl hydantoin, 1,3-dibromo-5,5-dimethyl hydantoin, sulfuryl chloride, quaternary ammonium perhalides (containing chlorine, bromine or iodine), cupric bromide or cupric chloride, N-chloro-phthalimide, pyridine perchloride, pyridine or pyrrolidone perbromide, pyridine or pyrrolidone periodide, hexachloro-2,4-cyclohexadienone, tert-butyl hypochlorite, trichloroisocyanuric acid, trichloromethane sulfonyl halogenide and iodine monochloride. Among them, quaternary ammonium perhalides containing chlorine, bromine or iodine (e.g., benzyl trimethylammonium tribromide and benzyl trimethylammonium triiodide) and pyridine perhalides containing chlorine, bromine or iodine (e.g., pyridinium bromide perbromide) are preferred, and benzyl trimethylammonium tribromide is more preferred. Iodine monochloride is also preferred.

Halogenation may be implemented via a lithiated intermediate. The amount of the halogenating agent is not particularly limited but may be 1 to 100 mol, preferably 1 to 10 mol, more preferably 1 mol to 5 mol, relative to 1 mol of a compound of the general formula (3). In the case that there exist two reaction sites, 2 times the molar amount may be used.

In implementing a reaction for obtaining a compound represented by the general formula (1), a solvent may be used or may not be used. An ordinary solvent used in synthesis of organic compounds may be used. Examples of the solvent include: an aromatic compound having no methyl group such as chlorobenzene, o-dichlorobenzene, bromobenzene and nitrobenzene; a saturated aliphatic hydrocarbon such as n-hexane, n-heptane and n-pentane; an alicyclic hydrocarbon such as cyclohexane, cycloheptane, cyclopentane; a saturated aliphatic halogenated hydrocarbon such as n-propyl bromide, n-butyl chloride, n-butyl bromide, dichloromethane, dibromomethane, dichloropropane, dibromopropane, dichloroethane, dibromoethane, dichloropropane, dibromopropane, dichlorobutane, chloroform, bromoform, carbon tetrachloride, carbon tetrabromide, trichloroethane, tetrachloroethane and pentachloroethane; a halogenated cyclic hydrocarbon such as chlorocyclohexane, chlorocyclopentane and bromocyclopentane; an ester such as ethyl acetate, propyl acetate, butyl acetate, methyl propionate, ethyl propionate, propyl propionate, butyl propionate, methyl butyrate, ethyl butyrate, propyl butyrate and butyl butyrate; and a ketone such as acetone, methyl ethyl ketone and methyl isobutyl ketone. These solvents may be used alone or two or more thereof may be mixed. Preferably the solvent has a melting point at room temperature or lower, so that they are in a liquid state during a low-temperature reaction.

The amount of the solvent is not particularly limited but may be about 0 to 10000 mol relative to 1 mol of a compound of the general formula (3).

The reaction may be implemented at a temperature of −100° C. to 100° C. The reaction temperature may be, as appropriate, changed in this range. The range may be preferably −78° C. to 50° C., more preferably −50° C. to 30° C. In this reaction, the reaction time may be normally 10 minutes to 1000 hours, preferably 30 minutes to 100 hours, more preferably 30 minutes to 10 hours. In order to complete the reaction in a short time, the reaction temperature, the halogenating agent and the amount of the solvent may be adjusted.

If necessary, a substance of interest may be isolated from a reaction mixture and purified by known isolation and purification methods. A high-purity compound is required for use as an organic semiconductor in many cases. In that case, known methods such as recrystallization, column chromatography and vacuum sublimation purifying may be employed. As appropriate, the methods may be combined for purification.

In the case that $Z_1$ is a hydrogen atom, a compound of the general formula (3) may be halogenated directly or via lithiation so as to produce a compound of the general formula (1).

In the case that $Z_1$ is a leaving group, an elimination reaction of the leaving group is not limited but may be implemented, for instance, as described in Non Patent Literature 7. Examples of the elimination agent (for example, a desilylation agent for desilylation) include various acids such as hydrochloric acid, acetic acid and para-toluenesulfonic acid; and fluoride ions such as tetrabutylammonium fluoride, hydrofluoric acid and cesium fluoride. Fluoride ions such as tetrabutylammonium fluoride, hydrofluoric acid and cesium fluoride are preferred.

In this reaction, the amount of the fluoride ions are not particularly limited but may be 0.1 to 10 mol, preferably 1 to 5 mol, more preferably 1 mol to 2 mol, relative to 1 mol of a compound of the general formula (3) having a silyl alkyl group. In the case that there exist two reaction sites, 2 times the molar amount may be used.

In the elimination reaction, a solvent may be used or may not be used. An ordinary solvent used in synthesis of organic compounds may be used. Examples of the solvent include: ethers such as diethyl ether, anisole and tetrahydrofuran; amides such as dimethylacetamide and dimethylformamide; nitriles such as acetonitrile, propionitrile and benzonitrile;

alkanes such as hexane, cyclohexane and octane; and alcohols such as methanol, ethanol and butanol. Ethers such as tetrahydrofuran are preferred. The amount of the solvent is not particularly limited but may be about 0 to 10000 mol relative to 1 mol of a compound of the general formula (3). The reaction may be implemented at a temperature of −80° C. to 200° C. The reaction temperature may be, as appropriate, changed in this range. The range may be preferably −50° C. to 100° C., more preferably −40° C. to 80° C. In this reaction, the reaction time may be 1 minute to 10 hours, and the reaction is completed preferably in a short time. The reaction time may be normally 5 minutes to 20 hours, preferably 10 minutes to 10 hours. In order to complete the reaction in a short time, the reaction temperature, the elimination agent and the amount of the solvent may be adjusted.

A compound represented by the general formula (3) wherein Z1 is a hydrogen atom may be halogenated directly or via lithiation so as to produce a compound of the general formula (1).

In this reaction, the halogenation method may be the same as that applied to a compound of general formula (3) wherein a leaving group recited in Z1 is a trialkylsilyl group. A halogenation method via an intermediate lithiated in a solvent is preferred.

Examples of the solvent for use in the reaction specifically include ethers such as diethyl ether, anisole and tetrahydrofuran; amides such as dimethylacetamide and dimethylformamide; nitriles such as acetonitrile, propionitrile and benzonitrile; alkanes such as hexane, cyclohexane and octane; and alcohols such as methanol, ethanol and butanol. Ethers such as tetrahydrofuran are preferred. The amount of the solvent is not particularly limited but may be about 0 to 10000 mol relative to 1 mol of a compound of the general formula (3). The reaction may be implemented at a temperature of −80° C. to 200° C. The reaction temperature may be, as appropriate, changed in this range. The range may be preferably −50° C. to 100° C., more preferably −40° C. to 80° C. In this reaction, the reaction time may be normally 1 minute to 10 hours, preferably 30 minutes to 20 hours, more preferably 1 hour to 10 hours. In order to complete the reaction in a short time, preferably the reaction temperature, the lithiation agent, the halogenating agent and the amount of the solvent are adjusted.

In each reaction, if necessary, a substance of interest may be isolated from a reaction mixture and purified by known isolation and purification methods. Known methods such as recrystallization, column chromatography, and vacuum sublimation purifying may be employed. As appropriate, the methods may be combined for purification.

A compound represented by the general formula (3) is preferably produced by ring-closing condensation of a compound represented by the general formula (4) and a compound represented by the general formula (5). The reaction may be implemented in accordance with the descriptions in Non Patent Literatures 8 and 9. When there exist two or more reaction sites in a molecule, ring-closing condensation reactions may be implemented at the two or more sites in parallel.

More specifically, the product may be obtained by mixing a compound represented by the general formula (4) and a compound represented by the general formula (5) in an organic solvent to react them.

The ratio of a compound represented by the general formula (5) to a compound represented by the general formula (4) is not particularly limited but may be 0.5 to 5 mol, preferably 0.9 to 3 mol, more preferably 1 to 2 mol, relative to 1 mol of the compound represented by the general formula (4). In the case that there are two reaction sites, 2 times the molar amount may be used.

An ordinary solvent used in organic synthesis may be used for the solvent. Examples of the solvent include: an aromatic compound having no methyl group such as chlorobenzene, o-dichlorobenzene, bromobenzene and nitrobenzene; a saturated aliphatic hydrocarbon such as n-hexane, n-heptane and n-pentane; an alicyclic hydrocarbon such as cyclohexane, cycloheptane and cyclopentane; a saturated aliphatic halogenated hydrocarbon such as n-propyl bromide, n-butyl chloride, n-butyl bromide, dichloromethane, dibromomethane, dichloropropane, dibromopropane, dichloroethane, dibromoethane, dichloropropane, dibromopropane, dichlorobutane, chloroform, bromoform, carbon tetrachloride, carbon tetrabromide, trichloroethane, tetrachloroethane and pentachloroethane; a halogenated cyclic hydrocarbon such as chlorocyclohexane, chlorocyclopentane and bromocyclopentane; an ester such as ethyl acetate, propyl acetate, butyl acetate, methyl propionate, ethyl propionate, propyl propionate, butyl propionate, methyl butyrate, ethyl butyrate, propyl butyrate and butyl butyrate; and a ketone such as acetone, methyl ethyl ketone and methyl isobutyl ketone. These solvents may be used alone or two or more thereof may be mixed. The amount of the solvent is not particularly limited but may be about 0 to 10000 mol relative to 1 mol of a compound of the general formula (4). The reaction may be implemented at a temperature of −80° C. to 200° C. The reaction temperature may be, as appropriate, changed within this range. The range may be preferably −50° C. to 100° C., more preferably −40° C. to 80° C. In this reaction, the reaction time is may be normally 1 minute to 10 hours, preferably 5 minutes to 20 hours, more preferably 10 minutes to 10 hours. In order to complete the reaction in a short time, the reaction temperature and the amount of the solvent may be adjusted.

In this reaction, if necessary, a substance of interest may be isolated from a reaction mixture and purified by known isolation and purification methods. Known methods such as recrystallization, column chromatography and vacuum sublimation purifying may be employed. As appropriate, the methods may be combined for purification.

The compounds of the general formulae (1), (3), (4) and (5) may be used as intermediates or raw materials for producing compounds of the general formula (2). Several examples of the combinations thereof are shown below, but the present invention is not limited thereto.

The reaction paths for preparing Compounds (2-1), (2-19), (2-58), (2-73) and (2-112) by the manufacturing method of the present invention are shown in the following.

[Formula 22]

Synthesis path of compound (2-1)

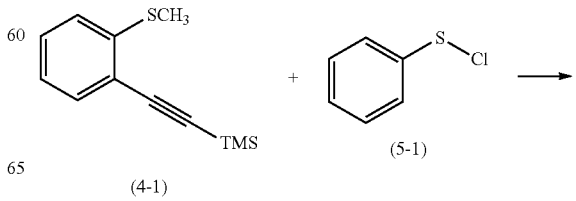

-continued
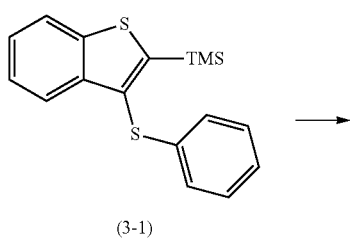
(3-1)
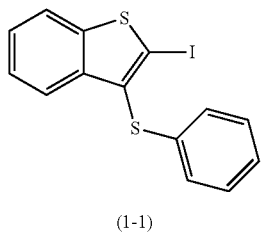
(1-1)
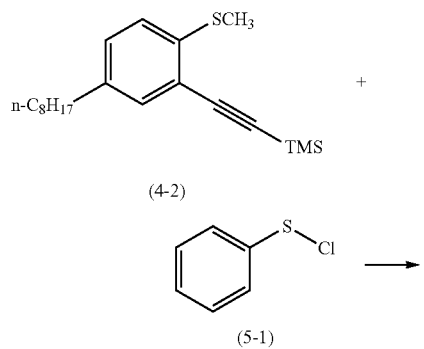
(2-1)
Synthesis path of compound (2-19)
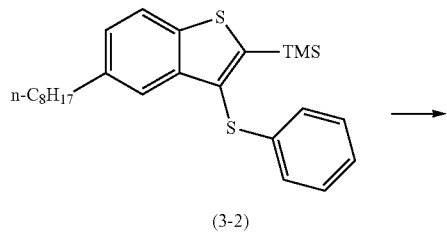
(4-2)
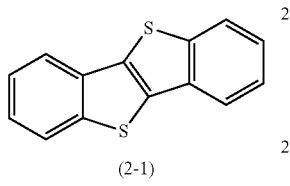
(5-1)
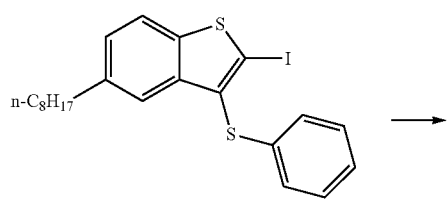
(3-2)
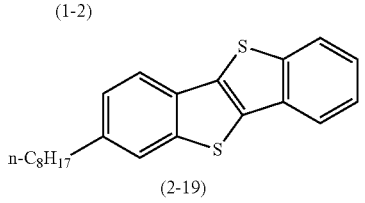
(1-2)
-continued
Synthesis path of compound (2-58)
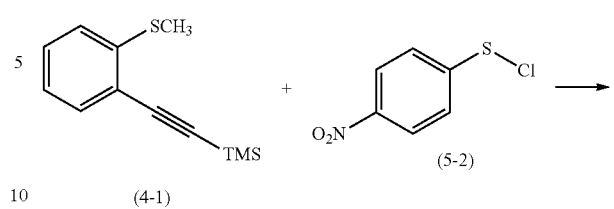
(4-1)    (5-2)
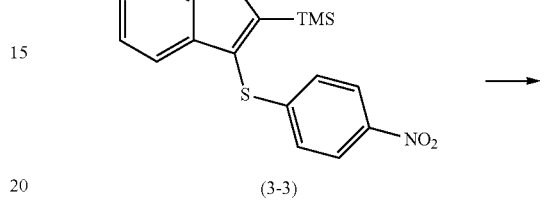
(3-3)
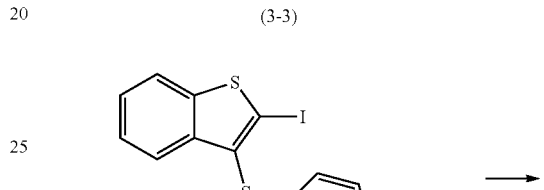
(1-3)
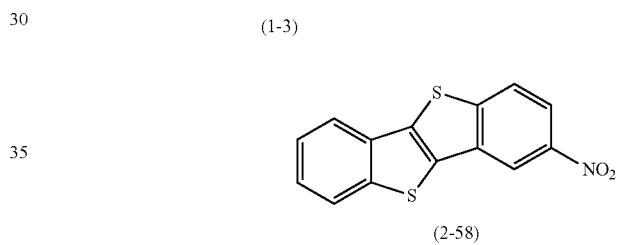
(2-58)
[Formula 23]
Synthesis path of compound (2-73)
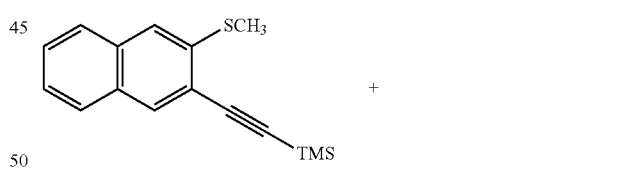
(4-3)
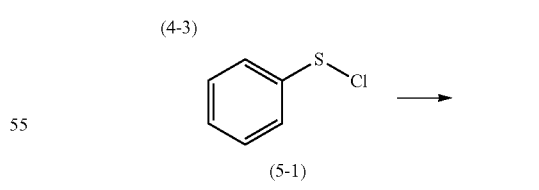
(5-1)
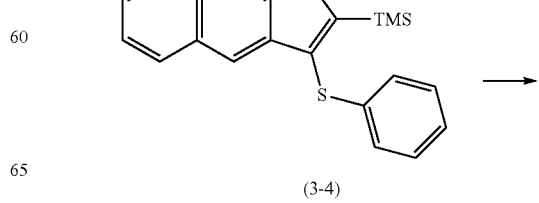
(3-4)

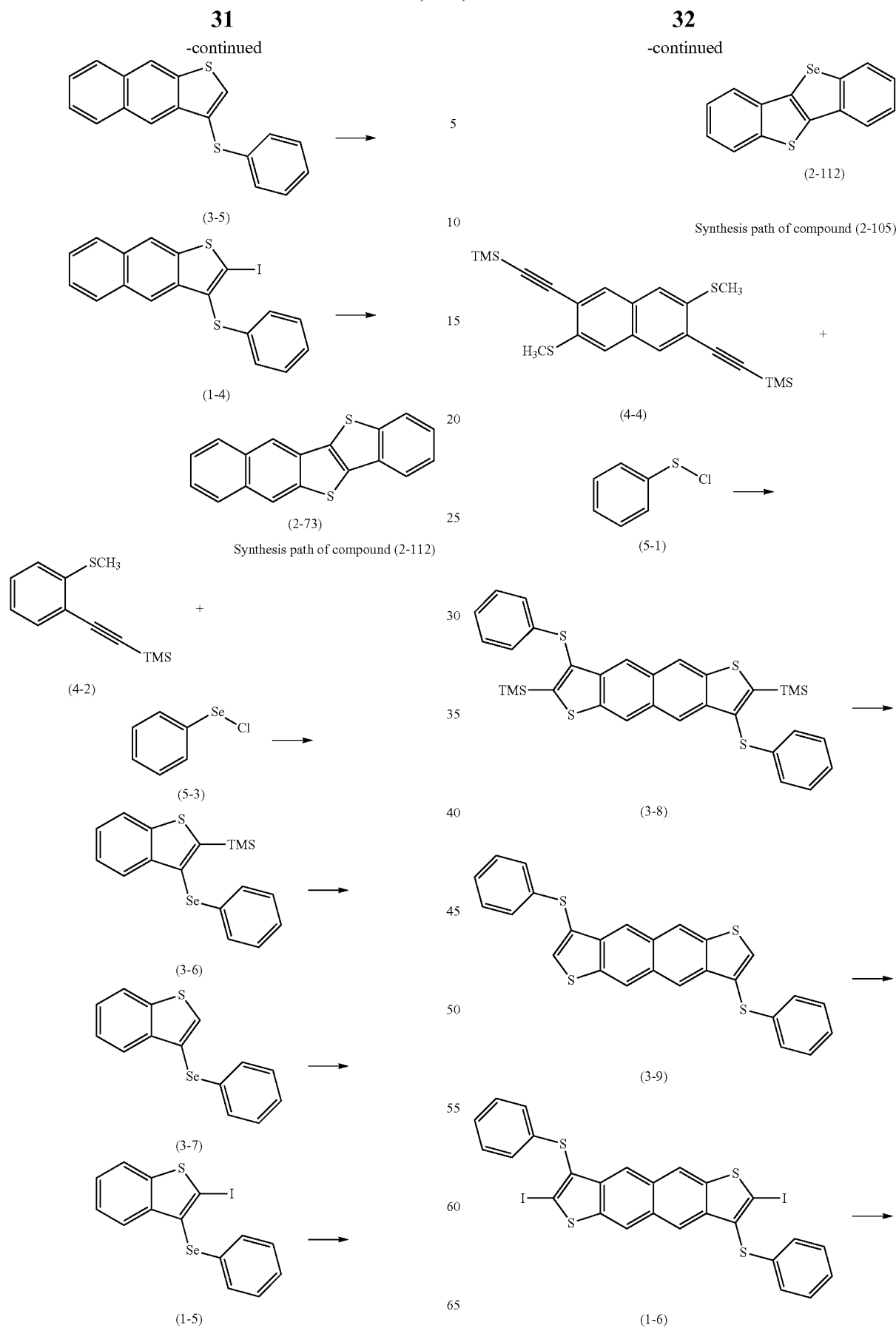

-continued

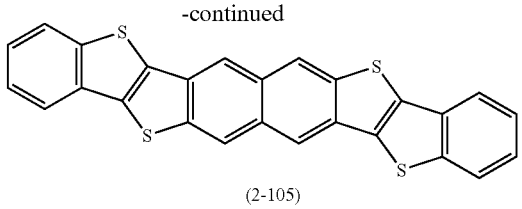

(2-105)

EXAMPLES

The present invention is described in further detail below with reference to Examples, but the present invention is not limited by the Examples.

The structure of a target compound was, as necessary, determined by 1H nuclear magnetic resonance spectrum (1H NMR), mass analysis spectrum (MS), melting point determination and element analysis. The apparatuses for use were as follows.

$^1$H NMR: JEOL LAMBDA 400 spectrometer
MS: Shimadzu QP-5050A
Melting point determination: Yanagimoto micro melting point apparatus MP-S3
Element analysis: Parkin Elmer 2400 CHN elemental analyzer

Example 1

Production of 3-(phenylsulfenyl)-2-trimethylsilyl-benzo[b]thiophene (Compound 3-1)

[Formula 24]

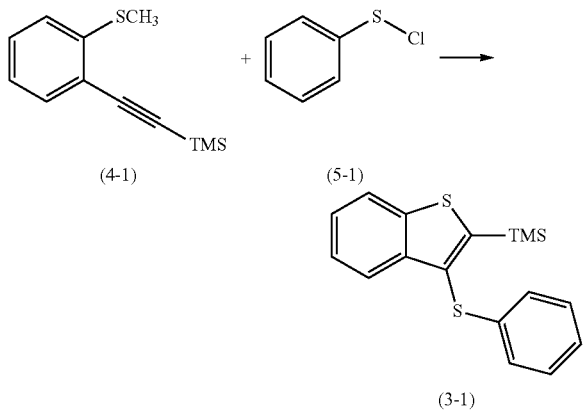

Under nitrogen atmosphere, a phenylsulfenyl chloride solution (1.5 eq, 0.7 ml, 7.5 mmol) in $CH_2Cl_2$ solvent (50 ml) was dripped into a $CH_2Cl_2$ solution (70 ml) of 2-(1-trimethylsilylethynyl)thioanisole (1.1 g, 5 mmol) at 0° C., and the mixture was stirred for 4 hours at room temperature. The reaction liquid was extracted with $CH_2Cl_2$ (10 ml), and washed with $H_2O$ (50 ml×3) and saline (50 ml). The extract liquid was dried with magnesium sulfate, and concentrated. Purification was implemented by column chromatography (silica gel, AcOEt:hexane=1:10, Rf: 0.80), so that 3-(phenylsulfenyl)-2-trimethylsilylbenzo[b]thiophene was produced (1.4 g, 4.5 mmol, yield: 93%).

$^1$H NMR (400 MHz, $CDCl_3$) δ 0.41 (s, 9H), 6.97 (t-d, 2H, J=1.42, 7.19 Hz), 7.05 (t-t, 1H, J=1.42, 7.19 Hz), 7.15 (d-t, 2H, 1.42, 7.19 Hz), 7.30 (d-t, 1H, J=1.32, 7.68 Hz), 7.35 (d-t 1H, J=1.32, 7.68 Hz), 7.73 (d-d, 1H, J=1.32, 7.68 Hz), 7.89 (d-d, 1H, J=1.32, 7.68 Hz)
EIMS (70 eV) m/z=134 (M$^+$)

Example 2

Production of 3-(phenylsulfenyl)-2-iodobenzo[b]thiophene (Compound 1-1)

[Formula 25]

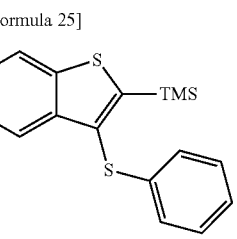

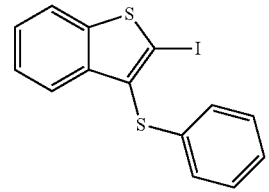

Under nitrogen atmosphere, a $CH_2Cl_2$ solution (0.6 ml, 0.6 mmol) of 1 M ICl was added into a $CH_2Cl_2$ solution (5 ml) of 3-(phenylsulfenyl)-2-trimethylsilylbenzo[b]thiophene (157 mg, 0.5 mmol) at −40° C. The mixture was stirred for 3 hours at 40° C., and then a $Na_2S_2O_5$ aqueous solution was added thereto. The mixture was extracted with $CH_2Cl_2$ (10 ml), and washed with saline (15 ml×3). The extract was dried with magnesium sulfate, and concentrated. Purification was implemented by column chromatography (silica gel, $CHCl_3$, Rf: 0.9), so that 3-(phenylsulfenyl)-2-iodobenzo[b]thiophene was produced (167 mg, 0.5 mmol, yield: 90%).

$^1$H NMR (400 MHz, $CDCl_3$) δ 7.08-7.14 (m, 3H), 7.20 (t, 2H, J=7.83 Hz), 7.28-7.35 (m, 2H), 7.79 (d-d, 2H, J=2.25, 6.94 Hz)
EIMS (70 eV) m/z=368 (M$^+$)

Example 3

Production of [1]benzothieno[3,2-b][1]benzothiophene (Compound 2-1)

[Formula 26]

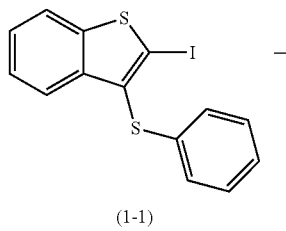

(1-1)

(2-1)

Under nitrogen atmosphere, into a degassed DMAc solution (8 ml) of 3-(phenylsulfenyl)-2-iodobenzo[b]thiophene (150 mg, 0.4 mmol) and NaOAc (67 mg, 0.8 mmol), $PdCl_2(PPh_3)_2$ (14 mg, 0.02 mmol) was added. The mixture was stirred for 12 hours at 140° C., and 1 N HCl was added to the reaction liquid. The mixture was extracted with EtOAc/hexane (50 ml), and washed with saline (50 ml×3). The extract was dried with magnesium sulfide, and concentrated. Purification was implemented by column chromatography (silica gel, hexane, Rf: 0.3), so that [1]benzothieno[3,2-b][1]benzothiophene was produced (72 mg, 0.3 mmol, yield: 73%).

$^1$H NMR (400 MHz, $CDCl_3$) δ 7.41 (d-t, 2H, J=1.42, 7.63 Hz), 7.47 (d-t, 2H, J=1.42, 7.63 Hz), 7.90 (d-d, 2H, J=1.42, 7.63 Hz), 7.93 (d-d, 2H, J=1.42, 7.63 Hz)

Example 4

Production of 3-((p-nitrophenyl)sulfenyl)-2-trimethylsilylbenzo[b]thiophene (Compound 3-3)

[Formula 27]

(4-1) + (5-2) → (3-3)

Except that phenylsulfenyl chloride was replaced with p-nitrophenylsulfenyl chloride, the reaction was implemented in the same way as in Example 1. Purification was implemented by column chromatography (silica gel, AcOEt:hexane=1:5, Rf: 0.83), so that 3-((p-nitrophenyl)sulfenyl)-2-trimethylsilylbenzo[b]thiophene was produced (yield: 97%).

$^1$H NMR (400 MHz, $CDCl_3$) δ 0.40 (s, 9H), 7.02 (d-d, 2H, J=2.15, 9.05 Hz), 7.35 (d-t, 1H, J=1.27, 7.48 Hz), 7.41 (d-t, 1H, J=1.27, 7.48 Hz), 7.68 (d-d, 1H, J=1.27, 7.48 Hz), 7.94 (d-d, 1H, J=1.27, 7.48 Hz), 8.01 (d-d, 2H, J=2.15, 9.05 Hz)

EIMS (70 eV) m/z=359 ($M^+$)

Example 5

Production of 3-((p-nitrophenyl)sulfenyl)-2-iodobenzo[b]thiophene (Compound 1-3)

[Formula 28]

(3-3) → (1-3)

Except that 3-(phenylsulfenyl)-2-trimethylsilylbenzo[b]thiophene was replaced with 3-((p-nitrophenyl)sulfenyl)-2-trimethylsilylbenzo[b]thiophene, the reaction was implemented in the same way as in Example 2. Purification was implemented by column chromatography (silica gel, $CHCl_3$, Rf: 0.9), so that a yellow solid was produced (yield: 94%).

$^1$H NMR (400 MHz, $CDCl_3$) δ 7.08 (t-d, 2H, J=2.01, 9.00 Hz), 7.34 (d-d, 1H, J=1.03, 7.29 Hz), 7.38 (d-d, 1H, J=1.03, 7.29 Hz), 7.71 (d-d, 1H, J=1.22, 7.14 Hz), 7.84 (d-d, 1H, J=1.22, 7.14 Hz), 8.05 (t-d, 2H, J=2.01, 9.00 Hz)

EIMS (70 eV) m/z=418 ($M^+$)

Example 6

Production of 3-nitro[1]benzothieno[3,2-b][1]benzothiophene (Compound 2-58)

[Formula 29]

(1-3) → (2-58)

Except that 3-(phenylsulfenyl)-2-iodobenzo[b]thiophene was replaced with 3-((p-nitrophenyl)sulfenyl)-2-iodobenzo

[b]thiophene, the reaction was implemented in the same way as in Example 3. Purification was implemented by column chromatography (silica gel, CHCl₃, Rf: 0.9), so that a yellow solid was produced (yield: 81%).

¹H NMR (400 MHz, CDCl₃) δ 7.48 (d-t, 1H, J=1.61, 7.19 Hz), 7.51 (d-t, 1H, J=1.61, 7.19 Hz), 7.95 (m, 2H), 8.01 (d, 1H, J=8.85 Hz), 8.26 (d-d, J=2.2, 8.85 Hz), 8.77 (d, 1H, J=2.2 Hz)

Example 7

Production of 3-(phenylsulfenyl)-2-trimethylsilyl-naphtho[2,3-b]thiophene (Compound 3-4)

[Formula 30]

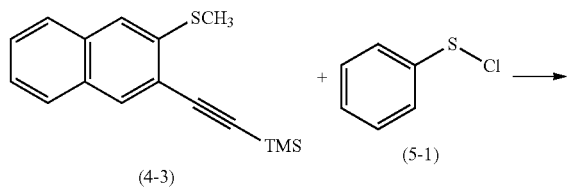

Except that 2-(1-trimethylsilylethynyl)thioanisole was replaced with 3-(1-trimethylsilylethynyl)-2-methylthionaphthalene, the reaction was implemented in the same way as in Example 1. Purification was implemented by column chromatography (silica gel, CHCl₃:hexane=1:5, Rf: 0.65), so that a white solid was quantitatively produced.

¹H NMR (400 MHz, CDCl₃) δ 0.44 (s, 9H), 7.00-7.07 (m, 3H), 7.15 (t-t, 2H, J=1.32, 7.58 Hz), 7.41 (d-t, 1H, J=1.22, 7.34 Hz), 7.47 (d-t, 1H, J=1.22, 7.34 Hz), 7.78 (d, 1H, J=8.22 Hz), 7.91 (d, 1H, J=8.22 Hz), 8.25 (s, 1H), 8.38 (s, 1H)

EIMS (70 eV) m/z=364 (M⁺)

Example 8

Production of 3-(phenylsulfenyl)naphtho[2,3-b]thiophene (Compound 3-5)

[Formula 31]

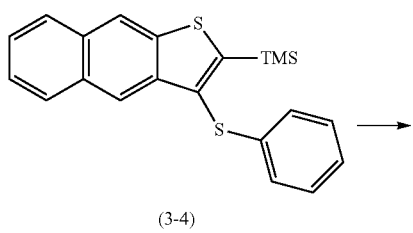

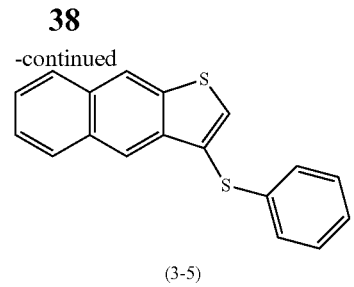

At −40° C., a THF solution (5 ml, 5 mmol) of 1 M tetra-n-butyl ammonium fluoride was added to THF (50 ml) and water (0.3 ml) of 3-(phenylsulfenyl)-2-trimethylsilylnaphtho[2,3-b]thiophene (550 mg, 1.5 mmol). After the mixture was stirred for 4 hours at room temperature, the reaction liquid was poured into water (50 ml). The precipitated solid was filtered and washed with ethanol and hexane. Purification was implemented by column chromatography (silica gel, CHCl₃, Rf: 0.9), so that a white solid was quantitatively produced.

¹H NMR (400 MHz, CDCl₃) δ 7.11-7.16 (m, 1H), 7.21 (d, 4H, J=4.35), 7.45 (d-t, 1H, J=1.37, 6.70 Hz), 7.50 (d-t, 1H, J=1.37, 6.70 Hz), 7.78 (s, 1H), 7.93 (d, 2H, 8.02), 8.31 (s, 1H), 8.39 (s, 1H)

Example 9

Production of 3-(phenylsulfenyl)-2-iodonaphtho[2,3-b]thiophene (Compound 1-4)

[Formula 32]

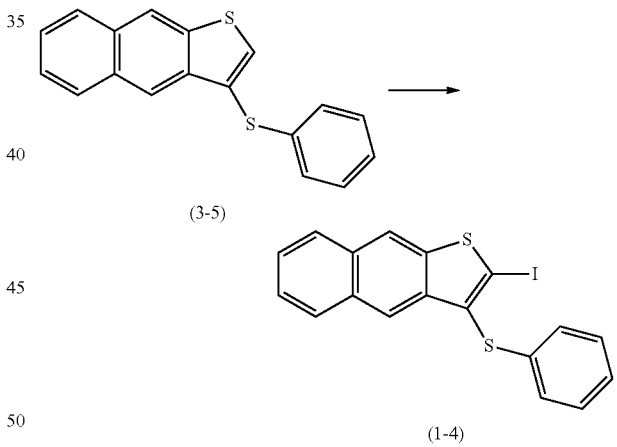

Under nitrogen atmosphere, n-butyl lithium (1.63 M (solvent: hexane), 0.46 ml, 0.75 mmol) was dripped into a THF solution (5 ml) of 3-(phenylsulfenyl)naphtho[2,3-b]thiophene (146 mg, 0.5 mmol) at 0° C. After the mixture was stirred for 1 hour at room temperature, iodine (190 mg, 0.75 mmol) was added thereto at 0° C. and the mixture was stirred for further 6 hours at room temperature. Subsequently an aqueous solution of Na₂S₂O₅ was added thereto, and the mixture was extracted with CH₂Cl₂ (50 ml×3) and washed with saline (15 ml×3). The extract liquid was dried with magnesium sulfate, and concentrated. Purification was implemented by column chromatography (silica gel, CHCl₃, Rf: 0.9), so that 3-(phenylsulfenyl)-2-iodonaphtho[2,3-b]thiophene was produced as an orange solid (138 mg, 0.3 mmol, yield: 66%).

$^1$H NMR (400 MHz, CDCl$_3$) δ 7.10-7.22 (m, 5H), 7.46 (t, 1H, J=7.29 Hz), 7.51 (t, 1H, J=7.29 Hz), 7.91 (t, 2H, J=7.29 Hz), 8.28 (s, 1H), 8.30 (s, 1H)

Example 10

Production of [1]benzothieno[2,3-d]naphtho[2,3-b]thiophene (Compound 2-73)

[Formula 33]

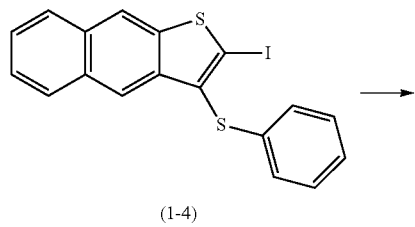

Except that 3-(phenylsulfenyl)-2-iodobenzo[b]thiophene was replaced with 3-(phenylsulfenyl)-2-iodonaphtho[2,3-b]thiophene, the reaction was implemented in the same way as in Example 3. Purification was implemented by column chromatography (silica gel, CHCl$_3$, Rf: 0.9), so that a yellow solid was produced (yield: 91%).

$^1$H NMR (400 MHz, CDCl$_3$) δ 7.44 (d-t, 1H, J=1.42, 7.39 Hz), 7.47 (d-t, 1H, J=1.42, 7.39 Hz), 7.51 (t, 1H, J=3.18 Hz), 7.53 (t, 1H, J=3.18 Hz), 7.89-7.97 (m, 2H), 8.01 (d, 1H, J=3.18 Hz), 8.04 (d, 1H, J=3.18 Hz), 8.37 (s, 1H), 8.40 (s, 1H)

Example 11

Production of 3-(phenylselenenyl)-2-trimethylsilyl-benzo[b]thiophene (Compound 3-6)

[Formula 34]

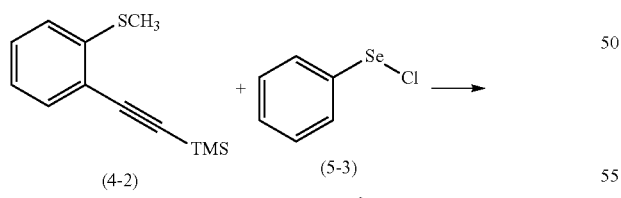

Except that phenylsulfenyl chloride was replaced with phenylselenenyl chloride, the reaction was implemented in the same way as in Example 1. Purification was implemented by column chromatography (silica gel, hexane, Rf: 0.50), so that 3-(phenylselenenyl)-2-trimethylsilybenzo[b]thiophene was quantitatively produced.

$^1$H NMR (400 MHz, CDCl$_3$) δ 0.43 (s, 9H), 7.05-7.14 (m, 5H), 7.31 (d-t, 1H, J=1.27, 7.04 Hz), 7.35 (d-t, 1H, J=1.27, 7.04 Hz), 7.82 (d-d, 1H, J=1.47, 7.24 Hz), 7.90 (d-d, 1H, J=1.47, 7.24 Hz)

EIMS (70 eV) m/z=362 (M$^+$)

Example 12

Production of 3-(phenylselenenyl)benzo[b]thiophene (Compound 3-7)

[Formula 35]

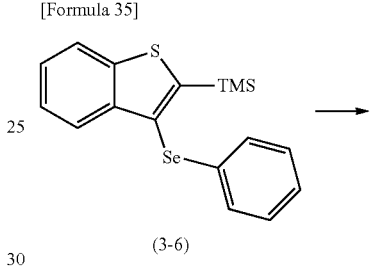

Except that 3-(phenylsulfenyl)-2-trimethylsilylnaphtho[2,3-b]thiophene was replaced with 3-(phenylselenenyl)-2-trimethylsilylbenzo[b]thiophene, the reaction was implemented in the same way as in Example 8. Purification was implemented by column chromatography (silica gel, CHCl$_3$, Rf: 0.9), so that a white solid was quantitatively produced.

Example 13

Production of 3-(phenylselenenyl)-2-iodobenzo[b]thiophene (Compound 1-5)

[Formula 36]

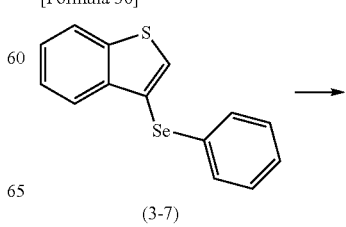

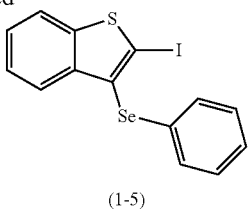

(1-5)

Except that 3-(phenylsulfenyl)naphtho[2,3-b]thiophene was replaced with 3-(phenylselenenyl)benzo[b]thiophene, the reaction was implemented in the same way as in Example 9.

Purification was implemented by column chromatography (silica gel, CHCl₃, Rf: 0.9), so that 3-(phenylselenenyl)-2-iodobenzo[b]thiophene was produced as a yellow solid (yield: 70%).

Example 14

Production of [1]benzoselenopheno[3,2-b][1]benzothiophene (Compound 2-112)

[Formula 37]

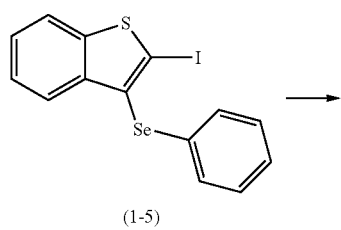

(1-5)

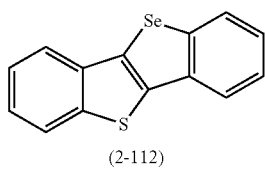

(2-112)

Except that 3-(phenylsulfenyl)-2-iodobenzo[b]thiophene was replaced with 3-(phenylselenenyl)-2-iodobenzo[b]thiophene, the reaction was implemented in the same way as in Example 3. Purification was implemented by column chromatography (silica gel, CHCl₃, Rf: 0.9), so that a yellow solid was produced (yield: 85%).

Example 15

Production of 3,7-bis(phenylsulfenyl)-2,6-bis(trimethylsilyl)naphtho[2,3-b:6,7-b']dithiophene (Compound 3-8)

[Formula 38]

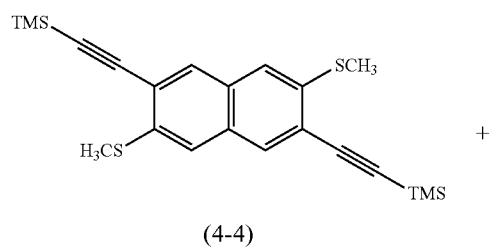

(4-4)

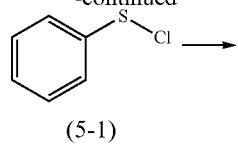

(5-1)

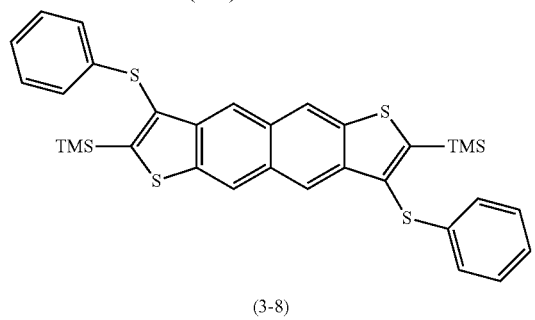

(3-8)

Except that 2-(1-trimethylsilylethylnyl)thioanisole was replaced with 3,7-bis(1-trimethylsilylethylnyl)-2,6-bis(methylthio)naphthalene, the reaction was implemented in the same way as in Example 1. Purification was implemented by column chromatography (silica gel, CHCl₃:hexane=1:5, Rf: 0.65), so that a yellow solid was produced (yield: 81%).

¹H NMR (400 MHz, CDCl₃) δ 0.43 (s, 9H), 7.02-7.08 (m, 3H), 7.15 (t, 2H, J=7.73 Hz), 8.31 (s, 1H), 8.41 (s, 1H)

Example 16

3,7-bis(phenylsulfenyl)naphtho[2,3-b:6,7-b']dithiophene (Compound 3-9)

[Formula 39]

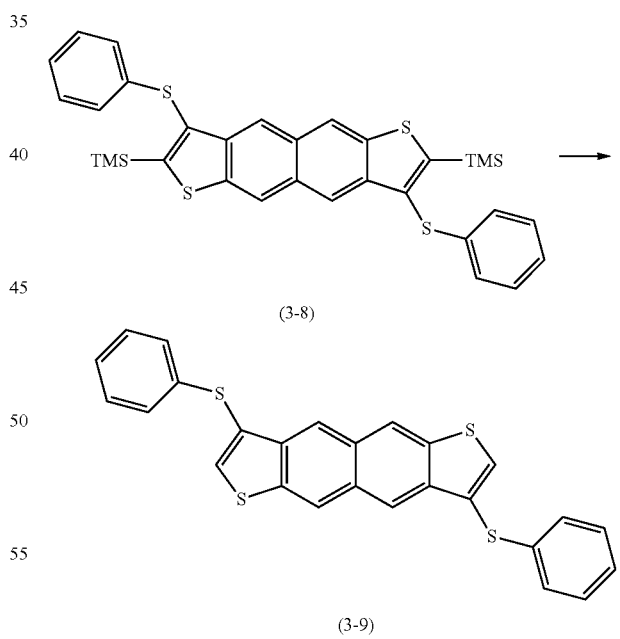

(3-8)

(3-9)

Except that 3-(phenylsulfenyl)-2-trimethylsilylnaphtho[2,3-b]thiophene was replaced with 3,7-bis(1-trimethylsilylethylnyl)-2,6-bis(methylthio)naphthalene, the reaction was implemented in the same way as in Example 8. Purification was implemented by column chromatography (silica gel, CHCl₃, Rf: 0.9), so that a yellow solid was quantitatively produced.

¹H NMR (400 MHz, CDCl₃) δ 7.12-7.24 (m, 10H), 7.78 (s, 2H), 8.37 (s, 1H), 8.47 (s, 1H)

Example 17

Production of 3,7-bis(phenylsulfenyl)-2,6-diiodenaphtho[2,3-b:6,7-b']dithiophene (Compound 1-6)

[Formula 40]

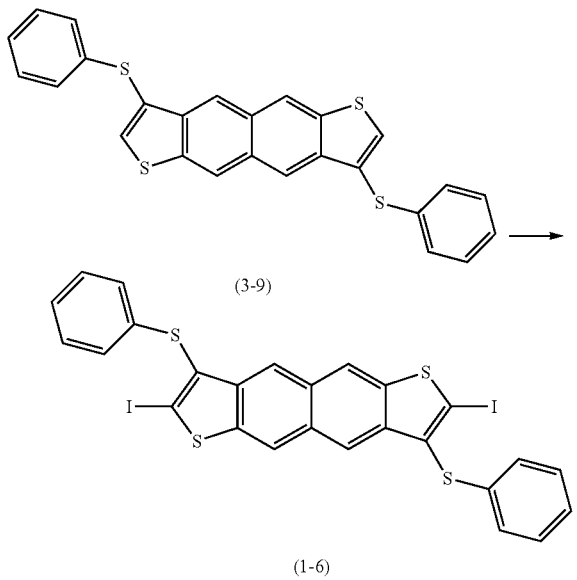

Under nitrogen atmosphere, n-butyl lithium (1.63 M hexane solution, 5.4 ml, 8.8 mmol) was dripped into a THF solution (100 ml) of 3,7-bis(phenylsulfenyl)naphtho[2,3-b:6,7-b']dithiophene (1.0 g, 2.2 mmol) at 0° C. After refluxing for 2 hours, iodine (2.23 g, 8.8 mmol) was added thereto at 0° C., and the mixture was refluxed for further 6 hours. Subsequently a $Na_2S_2O_5$ aqueous solution was added thereto at room temperature, and the mixture was diluted with water. The precipitated solid was filtered and washed with ethanol and chloroform, so that 3,7-bis(phenylsulfenyl)-2,6-diiodenaphtho[2,3-b:6,7-b']dithiophene was produced (570 mg, 0.8 mmol, yield: 37%).

$^1$H NMR (400 MHz, $CDCl_3$) δ 7.10-7.21 (m, 10H), 8.33 (s, 2H), 8.34 (s, 2H)

Example 18

Production of bis[1]benzothieno[2,3-d;2',3'-d']naphtho[2,3-b;6,7-b']dithiophene (Compound 2-105)

[Formula 41]

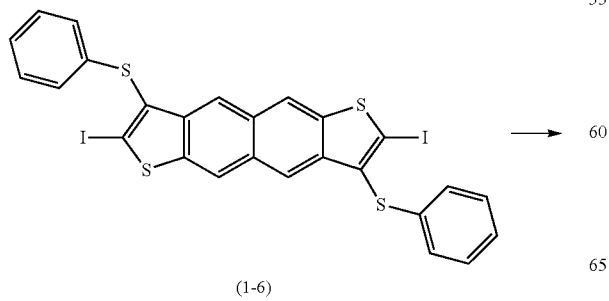

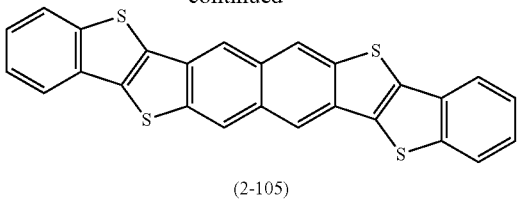

Under nitrogen atmosphere, into a degassed DMAc solution (60 ml) of 3,7-bis(phenylsulfenyl)-2,6-diiodonaphtho[2,3-b;6,7-b']dithiophene (600 mg, 0.85 mmol) and NaOAc (279 mg, 3.4 mmol), $PdCl_2(PPh_3)_2$ (63 mg, 0.09 mmol) was added. The mixture was stirred for 12 hours at 140° C., and 1 N HCl was added to the reaction liquid, which was diluted with water. The precipitated solid was filtered, washed with ethanol and chloroform, and further washed by soxhlet extraction using acetone and chloroform. Purification was implemented by sublimation purifying, so that a yellow solid was produced (130 mg, 0.29 mmol, yield: 34%).

As described above, a group of compounds having excellent organic semiconductor characteristics such as BTBT and DNTT derivatives can be conveniently and efficiently manufactured by the present invention. Furthermore, asymmetrical derivatives can be efficiently manufactured. Accordingly, it can be said that the present manufacturing method is extremely useful. Since a high-purity compound can be obtained at a high yield by the manufacturing method of the present invention, the product is suitable for use as an organic semiconductor.

The invention claimed is:

1. A method for manufacturing a heterocyclic compound represented by the general formula (2) from a heterocyclic compound represented by the general formula (1):

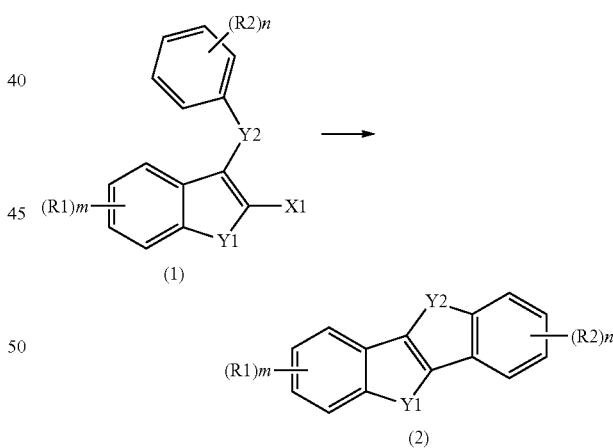

wherein X1 represents a halogen atom, Y1 and Y2 each independently represent an oxygen atom, a sulfur atom, or a selenium atom, R1 and R2 each independently represent a substituent, m and n each independently represent the number of R1 substituents and R2 substituents, respectively, wherein m and n are each an integer of 0 to 4, and when m is two or more, one of the R1 substituents may be the same or different from another of the R1 substituents, or one of the R1 substituents may be linked to another of the R1 substituents so as to form a ring which may have a substituent, and when n is two or more, one of the R2 substituents may be the same as or different from another of the R2 substituents, or one of the R2 substituents may be each linked to another of the R2 substituents so as to form a ring which may have a substituent, wherein said method comprises subjecting the compound of the general formula (1) to an intramolecular cyclization reaction.

2. The method according to claim 1, wherein the compound represented by the general formula (1) is obtained from a compound represented by the general formula (3):

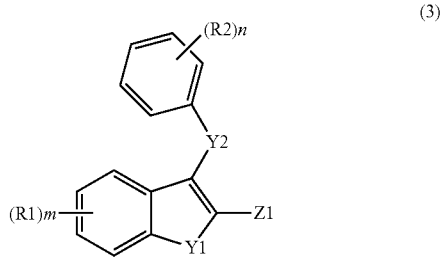

wherein Z1 represents a leaving group or a hydrogen atom, Y1 and Y2 each independently represent an oxygen atom, a sulfur atom, or a selenium atom, R1 and R2 each independently represent a substituent, and m and n each independently represent the number of R1 substituents and R2 substituents, respectively, wherein m and n are each an integer of 0 to 4, and when m is two or more, one of the R1 substituents may be the same or different from another of the R1 substituents, or one of the R1 substituents may be linked to another of the R1 substituents so as to form a ring which may have a substituent, and when n is two or more, one of the R2 substituents may be the same as or different from another of the R2 substituents, or one of the R2 substituents may be each linked to another of the R2 substituents so as to form a ring which may have a substituent.

3. The method according to claim 2, wherein the compound represented by the general formula (3) is obtained by reacting a compound represented by the general formula (4) and a compound represented by the general formula (5):

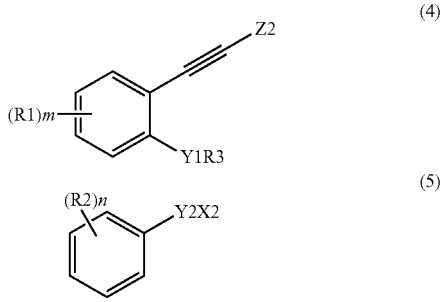

wherein Y1 and Y2 each independently represent an oxygen atom, a sulfur atom, or a selenium atom, R1 and R2 each independently represent a substituent, R3 represents a lower alkyl group, Z2 represents a leaving group, X2 represents a halogen atom, and m and n are as defined in claim 2.

4. The method according to claim 1, wherein Y1 and Y2 each independently represent a sulfur atom or a selenium atom.

5. The method according to claim 1, wherein R1 and R2 are each independently selected from the group consisting of a hydrogen atom, an alkyl group which may have a substituent, an aryl group which may have a substituent, an alkoxyl group which may have a substituent, a halogen atom, a nitro group, and a cyano group.

6. The method according to claim 1, wherein R1 and R2 are linked to each other so as to form a ring which may have a substituent.

7. The method according to claim 6, wherein the ring formed by linking R1 and R2 to each other which may have a substituent is a benzene ring which may have a substituent or a naphthalene ring which may have a substituent.

8. The method according to claim 2, wherein Y1 and Y2 each independently represent a sulfur atom or a selenium atom.

9. The method according to claim 3, wherein Y1 and Y2 each independently represent a sulfur atom or a selenium atom.

10. The method according to claim 2, wherein R1 and R2 are each independently selected from the group consisting of a hydrogen atom, an alkyl group which may have a substituent, an aryl group which may have a substituent, an alkoxyl group which may have a substituent, a halogen atom, a nitro group, and a cyano group.

11. The method according to claim 3, wherein R1 and R2 are each independently selected from the group consisting of a hydrogen atom, an alkyl group which may have a substituent, an aryl group which may have a substituent, an alkoxyl group which may have a substituent, a halogen atom, a nitro group, and a cyano group.

12. The method according to claim 4, wherein R1 and R2 are each independently selected from the group consisting of a hydrogen atom, an alkyl group which may have a substituent, an aryl group which may have a substituent, an alkoxyl group which may have a substituent, a halogen atom, a nitro group, and a cyano group.

13. The method according to claim 8, wherein R1 and R2 are each independently selected from the group consisting of a hydrogen atom, an alkyl group which may have a substituent, an aryl group which may have a substituent, an alkoxyl group which may have a substituent, a halogen atom, a nitro group, and a cyano group.

14. The method according to claim 9, wherein R1 and R2 are each independently selected from the group consisting of a hydrogen atom, an alkyl group which may have a substituent, an aryl group which may have a substituent, an alkoxyl group which may have a substituent, a halogen atom, a nitro group, and a cyano group.

15. The method according to claim 2, wherein R1 and R2 are linked to each other so as to form a ring which may have a substituent.

16. The method according to claim 3, wherein R1 and R2 are linked to each other so as to form a ring which may have a substituent.

17. The method according to claim 4, wherein R1 and R2 are linked to each other so as to form a ring which may have a substituent.

18. The method according to claim 8, wherein R1 and R2 are linked to each other so as to form a ring which may have a substituent.

19. The method according to claim 9, wherein R1 and R2 are linked to each other so as to form a ring which may have a substituent.

20. The method according to claim 15, wherein the ring formed by linking R1 and R2 to each other which may have a substituent is a benzene ring which may have a substituent or a naphthalene ring which may have a substituent.

21. The method according to claim 16, wherein the ring formed by linking R1 and R2 to each other which may have a substituent is a benzene ring which may have a substituent or a naphthalene ring which may have a substituent.

22. The method according to claim 17, wherein the ring formed by linking R1 and R2 to each other which may have a substituent is a benzene ring which may have a substituent or a naphthalene ring which may have a substituent.

23. The method according to claim 18, wherein the ring formed by linking R1 and R2 to each other which may have a substituent is a benzene ring which may have a substituent or a naphthalene ring which may have a substituent.

24. The method according to claim 19, wherein the ring formed by linking R1 and R2 to each other which may have a substituent is a benzene ring which may have a substituent or a naphthalene ring which may have a substituent.

* * * * *